US011104625B1

(12) United States Patent
Sofranko

(10) Patent No.: US 11,104,625 B1
(45) Date of Patent: Aug. 31, 2021

(54) OXIDATIVE CONVERSION OF HYDROCARBONS USING SULFUR OXIDES AS OXYGEN CARRIERS

(71) Applicant: Bio2Electric, LLC, Woburn, MA (US)

(72) Inventor: John A. Sofranko, Weston, MA (US)

(73) Assignee: Bio2Electric, LLC, Woburn, MA (US)

(*) Notice: Subject to any disclaimer, the term of this patent is extended or adjusted under 35 U.S.C. 154(b) by 0 days.

(21) Appl. No.: 16/877,992

(22) Filed: May 19, 2020

Related U.S. Application Data

(60) Provisional application No. 62/850,285, filed on May 20, 2019.

(51) Int. Cl.

| | |
|---|---|
| ***B01J 27/053*** | (2006.01) |
| ***C07C 5/48*** | (2006.01) |
| ***C07C 5/46*** | (2006.01) |
| ***C07C 11/04*** | (2006.01) |
| ***C07C 11/06*** | (2006.01) |
| ***B01J 37/28*** | (2006.01) |
| ***B01J 37/04*** | (2006.01) |
| ***B01J 37/02*** | (2006.01) |
| ***B01J 35/00*** | (2006.01) |
| ***B01J 37/00*** | (2006.01) |
| ***B01J 37/08*** | (2006.01) |
| ***B01J 27/055*** | (2006.01) |
| ***B01J 27/02*** | (2006.01) |

(52) U.S. Cl.
CPC ................. *C07C 5/48* (2013.01); *B01J 27/02* (2013.01); *B01J 27/053* (2013.01); *B01J 27/055* (2013.01); *B01J 35/002* (2013.01); *B01J 35/0033* (2013.01); *B01J 37/0036* (2013.01); *B01J 37/0201* (2013.01); *B01J 37/04* (2013.01); *B01J 37/08* (2013.01); *B01J 37/28* (2013.01); *C07C 5/46* (2013.01); *C07C 11/04* (2013.01); *C07C 11/06* (2013.01); *B01J 2523/10* (2013.01); *B01J 2523/11* (2013.01); *B01J 2523/12* (2013.01); *B01J 2523/13* (2013.01); *B01J 2523/14* (2013.01); *B01J 2523/15* (2013.01); *B01J 2523/20* (2013.01); *B01J 2523/21* (2013.01); *B01J 2523/22* (2013.01); *B01J 2523/23* (2013.01); *B01J 2523/24* (2013.01); *B01J 2523/25* (2013.01); *B01J 2523/62* (2013.01); *C07C 2521/02* (2013.01); *C07C 2523/02* (2013.01); *C07C 2527/053* (2013.01); *C07C 2527/054* (2013.01); *C07C 2527/055* (2013.01)

(58) Field of Classification Search
CPC ........... C07C 5/48; C07C 11/04; C07C 11/06; C07C 2521/02; C07C 2527/053; C07C 2527/054; C07C 2527/055; B01J 23/02; B01J 2523/10; B01J 2523/11; B01J 2523/12; B01J 2523/13; B01J 2523/14; B01J 2523/15; B01J 2523/20; B01J 2523/21; B01J 2523/22; B01J 2523/23; B01J 2523/24; B01J 2523/25; B01J 2523/62; B01J 35/002; B01J 35/0033; B01J 37/0036; B01J 37/04; B01J 37/28; B01J 37/0201; B01J 37/08; B01J 27/053; B01J 27/055; B01J 27/02
USPC ....... 502/216, 217, 218, 219, 220, 221, 222, 502/223
See application file for complete search history.

(56) References Cited

U.S. PATENT DOCUMENTS

| | | | | | |
|---|---|---|---|---|---|
| 2,493,038 | A | | 1/1950 | Snyder et al. | |
| 3,651,121 | A | | 3/1972 | Duke et al. | |
| 4,544,785 | A | * | 10/1985 | Withers | C07C 2/84 585/415 |
| 4,547,607 | A | | 10/1985 | Jones et al. | |
| 4,599,477 | A | | 7/1986 | Robinson et al. | |
| 4,670,619 | A | * | 6/1987 | Withers, Jr. | C07C 2/84 585/500 |
| 4,777,313 | A | * | 10/1988 | Sofranko | B01J 23/08 585/500 |
| 4,830,728 | A | | 5/1989 | Herbst et al. | |
| 5,026,947 | A | | 6/1991 | Mazurek | |
| 5,079,385 | A | | 1/1992 | Wu | |
| 5,091,163 | A | | 2/1992 | Gaffney et al. | |
| 5,192,809 | A | | 3/1993 | Jones et al. | |
| 5,545,787 | A | | 8/1996 | Cooper et al. | |
| 6,403,523 | B1 | | 6/2002 | Cantrell et al. | |
| 9,963,407 | B2 | | 5/2018 | Stije et al. | |
| 10,138,182 | B2 | * | 11/2018 | Sofranko | B01J 38/12 |
| 10,550,051 | B2 | | 2/2020 | Li et al. | |

(Continued)

FOREIGN PATENT DOCUMENTS

| | | | |
|---|---|---|---|
| EP | 2576046 | B1 | 11/2014 |
| EP | 2853521 | A1 | 4/2015 |

(Continued)

OTHER PUBLICATIONS

Anene et al., "Experimental Study of Thermal and Catalytic Pyrolysis of Plastic Waste Components", Sustainability, 2018, 10, 11 pages.

(Continued)

*Primary Examiner* — Elizabeth D Wood
(74) *Attorney, Agent, or Firm* — RatnerPrestia

(57) ABSTRACT

The oxidative coupling of methane (OCM) and the oxidative dehydrogenation (ODH) of ethane and higher hydrocarbons is described using $SO_3$ and sulfate, sulfite, bisulfite and metabifulfite salts as oxygen transfer agents in the presence of one or more elements selected from Groups 3 to 14 of the periodic table, optionally further in the presence of alkali or alkaline salts and/or sulfur-containing compounds.

11 Claims, 2 Drawing Sheets

(56) References Cited

U.S. PATENT DOCUMENTS

| | | | | |
|---|---|---|---|---|
| 2003/0181325 | A1* | 9/2003 | Ou | B01J 23/34 502/302 |
| 2005/0124841 | A1 | 6/2005 | Rapier et al. | |
| 2011/0245571 | A1 | 10/2011 | Kustov et al. | |
| 2012/0041246 | A1 | 2/2012 | Scher et al. | |
| 2012/0203042 | A1 | 8/2012 | Huber et al. | |
| 2014/0275667 | A1 | 9/2014 | Sarker | |
| 2014/0371504 | A1 | 12/2014 | Stine et al. | |
| 2016/0122264 | A1 | 5/2016 | Olbert et al. | |
| 2017/0226030 | A1 | 8/2017 | Li et al. | |
| 2019/0022626 | A1 | 1/2019 | Schammel et al. | |
| 2019/0315667 | A1 | 10/2019 | Sofranko et al. | |
| 2020/0215515 | A1 | 7/2020 | Li et al. | |

FOREIGN PATENT DOCUMENTS

| | | | |
|---|---|---|---|
| WO | 2014202501 | A1 | 12/2014 |
| WO | 2016049144 | A9 | 3/2016 |
| WO | 2018005456 | A1 | 1/2018 |
| WO | 2018049389 | A1 | 3/2018 |
| WO | 2018157042 | A1 | 8/2018 |
| WO | 2018232133 | A1 | 12/2018 |

OTHER PUBLICATIONS

Carey, J., "On the Brink of a Recycling Revolution?", PNAS, Jan. 24, 2017, vol. 114, No. 4, pp. 612-616.

Currao et al., "Understanding Zeolite Frameworks", Department of Chemistry and Biochemistry, University of Bern, 1965, 65 pages.

Elbadawi et al., "Kinetics of oxidative cracking of n-hexane to olefins over VO2/Ce—Al2—O3 under gas phase oxygen-free environment", http://onlinelibrary.wiley.com/doi/10.1002/aic.15491/abstract, 2016, 2 pages.

Lemonick, S., "Chemistry may have solutions to our plastic trash problem", Pollution, 2018, vol. 96, Iss. 25, 9 pages.

Olazar et al, "Light olefins from HDPE cracking in a two-step thermal and catalytic process", Chemical Engineering Journal, 207-208 (2012) pp. 27-34.

World Economic Forum, Ellen MacArthur Foundation, "The New Plastics Economy—Rethinking the Future of Plastics", http://ellenmacarthurfoundation.org/publications/the-new-plastics-economy-rethinking-the-future-of-plastics, 2014, 120 pages.

Boyadjian, C. et al., Catalytic oxidative cracking of hexane as a route to olefins, 2010, vol. 372, pp. 167-174, Applied Catalysis A: General.

Breck, D.W., General Introduction. Chapter 1, Zeolite Molecular Sieves: Structure, Chemistry, and Use, Wiley, 1974, 28 pages.

Davis, B., "Identification of Molecular Sieve Structures," 1989, pp. 282-347, Van Nostrand Reinhold Catalysis Series.

Fumoto, E., et al., "Production of Light Oil by Oxidative Cracking of Oil Sand Bitumen Iron Oxide Catalysts in a Steam Atmosphere," Energy Fuels, vol. 25, 2011, pp. 524-527.

Garcia, J.M., et al., "The future of plastics recycling," Science, Nov. 17, 2017, vol. 358(6365), 3 pages.

Ishihara, Y., et al., "Mechanism for gas formation in polyethylene catalytic decomposition." Polymer, 1992, vol. 33(16), pp. 3482-348.

Karge, et al., Post-Synthesis Modification I (Molecular Sieves), vol. 1, 2002, pp. 1-54.

Lee, H.W., et al., "Catalytic Pyrolysis Polyethylene and Ppolypropylene over Desilicated Beta and A1-MSU-F," 2018, Catalysts, vol. 8(501), pp. 1-15.

Manos, G., et al., "Catalytic Degradation of Hhigh-Density Polyethylene on an Ultrastable-Y Zeolite. Nature of Initial Polymer Reactions, Pattern of Formation of Gas and Liquid Products, and Temperature Effects," Industrial & Engineering Chemistry Research, Mar. 25, 2000, vol. 39(5), pp. 1203-1208.

Wu et al., "Hydrocarbon adsorption characterization of some high silica zeolites," pp. 547-554.

Marcilla, A., et al., "Study of the catalytic pyrolysis behavior of polyethylene-polypropylene mixtures," Journal of Analytical and Applied Pyrolysis, 2005, vol. 74, pp. 387-392.

Rahimi, A., et al., "Chemical recycling of waste plastics for new materials production," Jun. 7, 2017, Nature Reviews—Chemistry, vol. 1, Article 0046, pp. 1-11.

Seo, Y-H., et al., "Investigation of catalytic degradation of high-density polyethylene by hydrocarbon group type analysis," Journal of Analytical and Applied Pyrolysis,2003, vol. 70, pp. 383-398.

Szostak, R., Molecular Sieves—Principles of Synthesis and Identification, 17 pages, Van Nostrand Reinhold Catalysis Series, 1989.

Weitkamp, J., et al.,"Preparation of Oxide, Sulfide and Other Chalcogenide Clusters in Molecular Sieves," Molecular Sieves, 2002, vol. 3, pp. 339-414.

Sofranko et al., "Natural Gas to Gasoline. The ARCO GTG Process", Symposium on Methane Activation, Conversion and Utilization. International Congress of Pacific Basin Societes, Dec. 17-20, 1989, pp. 152.154.

Xu et al., "Combination of $CH_4$ Oxidatie Coupling Reaction with $C_{2H6}$ Oxidative Dehydrogenation by $CO_2$ to $C_2H_4$", 2002, Fuel, vol. 81, pp. 1593-1597.

Non Final Office Action for U.S. Appl. No. 16/846,815, dated Jun. 17, 2020, 15 pages.

Non Final Office Action for U.S. Appl. No. 16/800,883, dated Jun. 15, 2020, 30 pages.

Jordi Labs, "Typical Molecular Weights of Common Polymers", 2020 downloaded from https://jordilabs.com/blog/typical-polymer-molecular-weights, 5 pages.

Bovin et al., Electron Microscopy of Oxyborates. I. Defect Structure in the Minerals Pinakiolite, Ludwigite, Orthopinakiolite and Takéuchiite, 1981, Acta Cryst, vol. A37, pp. 28-35.

Kasper et al., "A New Structure Type For Metallic Oxides of Formula $A_6BO_3$". 1953, J. Chem. Phys., vol. 21, pp. 1897-1898.

Sofronova et al., "Ludwigites: From Natural Mineral to Modern Solid Solutions", 2017, Cryst. Res. Technol, vol. 52, No. 4, 19 pages.

De Vries et al., "The Thermal Decomposition of Potassium and Sodium-Pyrosulfate", J. Inorg. Nucl. Chem., 1968, vol. 31, pp. 1307-1313.

Neal et al., "Oxidative Dehydrogenation of Ethane: A Chemical Looping Approach", Energy Technology, 2016, vol. 4, pp. 1-10.

Sofranko et al., "The Oxidative Conversion of Methane to Higher Hydrocarbons", Journal of Catalysis, 1987, vol. 103, pp. 302-310.

Ding, N. et al., "Effect of hematite addition to $CaSO_4$ oxygen carrier in chemical looping combustion of coal char," 2015, vol. 5, pp. 56362-56376, RSC Advances, The Royal Society of Chemistry.

Li, H. et al., "Catalytic reduction of calcium sulfate to calcium sulfide by carbon monoxide," Aug. 3, 1999, vol. 38, pp. 3333-3337, Industrial & Engineering Chemistry Research.

Non Final Office Action for U.S. Appl. No. 16/888,066, dated Aug. 14, 2020, 27 pages.

Guo et al., "Recent Advances in $CaSO_4$ Oxygen Carrier for Chemical-Looping Combustion (CLC) Process", Chemical Engineering Communications, 2012, vol. 199, No. 11, pp. 1463-1491.

Meng et al., "Manganese Borides Synthesized at High Pressure and High Temperature", Journal of Applied Physics, 2013, vol. 111, 6 pages.

Non-Final Office Action for U.S. Appl. No. 17/110,941, dated Feb. 23, 2021, 51 pages.

Final Office Action for U.S. Appl. No. 16/800,883, dated Nov. 9, 2020, 32 pages.

* cited by examiner

OXIDATIVE CONVERSION OF HYDROCARBONS USING SULFUR OXIDES AS OXYGEN CARRIERS

CROSS REFERENCE TO RELATED APPLICATIONS

This application claims the benefit of and priority from U.S. Provisional Application No. 62/850,285, filed on May 20, 2019, the disclosure of which is incorporated by reference herein in its entirety for all purposes.

TECHNICAL FIELD

The present disclosure relates to the oxidative coupling of methane (OCM) and the oxidative dehydrogenation (ODH) of ethane and higher saturated hydrocarbons using sulfur oxides as oxygen transfer agents.

BACKGROUND

Ethylene and propylene are important building blocks for the petrochemical industry and are used in manufacturing polymers such as polyethylene, polypropylene, polystyrene and additional chemical compounds of commercial interest. Over 90% of the global olefin production originates from the high temperature steam cracking of naphtha or ethane and propane. The steam cracking process, which utilizes furnaces, is highly energy intensive, and 1.5 to 2 tons of carbon dioxide are produced for every ton of olefin product.

Natural gas production from shale deposits has dramatically increased supply in recent years. As a result of the continued global demand for olefins and the potential for a new growing supply of ethane and propane available in natural gas liquids from shale deposits, a significant amount of interest and investment is currently directed to expanding the capacity of ethylene and propylene derived from these new sources. Numerous olefin grass root and expansion projects are either under contract or in the planning stages to take advantage of the relatively low cost liquids from wet shale gas. However, there are several environmental and cost challenges to operating at this level of new capacity.

Olefin production is the largest emitter of $CO_2$ and NOR in the organic chemical industry. With worldwide ethylene production at approximately 150 MT/yr, the industry emits 150-300 MT/yr of $CO_2$ and around 1.4 MT/yr of NOR. Projects located in strict EPA non-attainment zones are challenged by the increased cost of NOR control. The total greenhouse gas (GHG) emission profile, reported in $CO_2$ equivalents, is another critical part of the permitting process for all production expansions.

The industry continues to push for a production technology that: (1) generates higher overall yields of ethylene and propylene; (2) increases the run length time between furnace turnarounds (e.g., inspections, repairs, improvements, etc.); (3) lowers steam and energy utilization; and (4) lowers all GHGs, including carbon dioxide and NOx. The ODH of ethane and propane to ethylene and propylene, respectively, offers a potential solution for addressing these needs, such as a production route that can significantly reduce $CO_2$ emissions and virtually eliminate NOx emissions from world scale plants.

The ODH of ethane is a selective catalytic process that produces primarily ethylene and water as products in an exothermic reaction (reaction 1).

$$CH_3CH_3+\tfrac{1}{2}O_2 \rightarrow CH_2CH_2+H_2O \quad \Delta H_o=-105 \text{ kJ/mol} \qquad (1)$$

The per pass yield of the ODH reaction is not limited by thermodynamic equilibrium, as it is in pyrolysis (reaction 2).

$$CH_3CH_3+\text{Heat} \leftrightarrows CH_2CH_2+H_2 \quad \Delta H_o=+137 \text{ kJ/mol} \qquad (2)$$

ODH provides an opportunity to improve the efficiency of olefin production. While a significant amount of research has been done over the last 25 years, most reported ODH processes are not cost-effective because they involve highly exothermic catalytic reactions with co-fed oxygen and platinum group metal catalysts. Thus, there is a significant need for improved materials for facilitating ODH, as well as reactors and processes that incorporate these improved materials.

The oxidative coupling of methane (OCM) and the oxidative dehydrogenation (ODH) of ethane and higher hydrocarbons to olefinic products represent reactions of substantial commercial value. These conversions may be accomplished (i) catalytically, by reacting a hydrocarbon and an oxygen-containing gas in the presence of a catalyst, or by (ii) a redox oxygen transfer mode whereby a hydrocarbon is reacted with an Oxygen Transfer Agent (OTA) which supplies the oxygen needed for the formation of water. Both systems are exemplified by the following reaction (reaction 3).

$$zC_nH_{2n+2-2\beta}+(z-1+\delta)\text{“O”} \rightarrow C_{(z\times n)}H_{2(z\times n)+2-2\beta-2\delta}+(z-1+\delta)H_2O \qquad (3)$$

where z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation. The oxygen “O” may be supplied by the reduction of a metal oxide transfer agent or via molecular oxygen in the presence of a suitable catalyst. The agent that supplies the oxygen, whether a reducible metal oxide or another type of catalyst or catalyst system may be referred to as an oxygen transfer agent (OTA).

A commercially viable catalyst or oxygen transfer agent (OTA) should have at least the following attributes:

- an ability to achieve a high rate of conversion of the feedstock to desired products;
- highly selective for the desired products and in high yields;
- having a high oxygen carrying capacity;
- produced at low cost from readily available materials; and
- exhibits a viable high temperature particle flow and fluidization and low attrition.

There remains a need for catalysts and OTAs that satisfy these requirements, especially for use in the oxidative coupling of methane (OCM) and the oxidative dehydrogenation (ODH) of ethane and higher hydrocarbons.

SUMMARY

An aspect of the invention is a method of oxidatively dehydrogenating a saturated hydrocarbon feed to produce a dehydrogenated (unsaturated) hydrocarbon product and water, the method comprising:

contacting the saturated hydrocarbon feed at the same or different times with (a) at least one oxygen transfer agent comprising a sulfate salt, such as a sulfate salt of an alkali or alkaline earth metal;

(b) one or more elements selected from Groups 3 to 14 of the periodic table;

(c) optionally an alkali or alkaline earth metal salt that is not the sulfate salt of (a); and (d) optionally a sulfur-containing compound that is not the sulfate salt of (a);

and oxidatively dehydrogenating the hydrocarbon feed under suitable reaction conditions to produce the dehydrogenated hydrocarbon product and the water.

Another aspect of the invention is a method of oxidatively dehydrogenating a saturated hydrocarbon feed to produce a dehydrogenated (unsaturated) hydrocarbon product and water, the method comprising:

contacting the saturated hydrocarbon feed at the same or different times with (a) at least one oxygen transfer agent comprising $SO_3$;

(b) optionally one or more elements selected from Groups 3 to 14 of the periodic table;

(c) optionally an alkali or alkaline earth metal salt; and (d) optionally a sulfur-containing compound that is not $SO_3$; and oxidatively dehydrogenating the hydrocarbon feed under suitable reaction conditions to produce the dehydrogenated hydrocarbon product and the water.

An aspect of the invention is a method of oxidatively dehydrogenating a saturated hydrocarbon feed to produce a dehydrogenated (unsaturated) hydrocarbon product and water, the method comprising:

contacting the saturated hydrocarbon feed at the same or different times with (a) at least one oxygen transfer agent comprising a sulfite, bisulfite and/or metabisulfite salt, such as a sulfite, bisulfite and/or metabisulfite salt of an alkali or alkaline earth metal;

(b) one or more elements selected from Groups 3 to 14 of the periodic table;

(c) optionally an alkali or alkaline earth metal salt that is not the sulfite, bisulfite and/or metabisulfite salt of (a); and (d) optionally a sulfur-containing compound that is not the sulfite, bisulfite and/or metabisulfite salt of (a); and oxidatively dehydrogenating the hydrocarbon feed under suitable reaction conditions to produce the dehydrogenated hydrocarbon product and the water.

Another aspect of the invention is an apparatus configured to produce a dehydrogenated (unsaturated) hydrocarbon product by oxidative dehydrogenation of a saturated hydrocarbon feed to produce the dehydrogenated hydrocarbon product and water, the apparatus comprising:

at least one vessel configured for:

(i) contacting the saturated hydrocarbon feed at the same or different times with (a) at least one oxygen transfer agent comprising a sulfate salt, such as a sulfate salt of an alkali or alkaline earth metal;

(b) one or more elements selected from Groups 3 to 14 of the periodic table;

(c) optionally an alkali or alkaline earth metal salt that is not the sulfate salt of (a); and (d) optionally a sulfur-containing compound that is not the sulfate salt of (a);

and (ii) oxidatively dehydrogenating the saturated hydrocarbon feed under suitable reaction conditions to produce the dehydrogenated hydrocarbon product and the water, wherein at least a portion of the oxygen transfer agent is converted to a reduced form.

Another aspect of the invention is an apparatus configured to produce a dehydrogenated (unsaturated) hydrocarbon product by oxidative dehydrogenation of a saturated hydrocarbon feed to produce the dehydrogenated hydrocarbon product and water, the apparatus comprising:

at least one vessel configured for:

(i) contacting the saturated hydrocarbon feed at the same or different times with (a) at least one oxygen transfer agent comprising $SO_3$;

(b) optionally one or more elements selected from Groups 3 to 14 of the periodic table;

(c) optionally an alkali or alkaline earth metal salt; and (d) optionally a sulfur-containing compound that is not $SO_3$; and (ii) oxidatively dehydrogenating the saturated hydrocarbon feed under suitable reaction conditions to produce the dehydrogenated hydrocarbon product and the water, wherein at least a portion of the oxygen transfer agent is converted to a reduced form.

Another aspect of the invention is an apparatus configured to produce a dehydrogenated (unsaturated) hydrocarbon product by oxidative dehydrogenation of a saturated hydrocarbon feed to produce the dehydrogenated hydrocarbon product and water, the apparatus comprising:

at least one vessel configured for:

(i) contacting the saturated hydrocarbon feed at the same or different times with (a) at least one oxygen transfer agent comprising a sulfite, bisulfite and/or metabisulfite salt, such as a sulfite, bisulfite and/or metabisulfite salt of an alkali or alkaline earth metal;

(b) one or more elements selected from Groups 3 to 14 of the periodic table;

(c) optionally an alkali or alkaline earth metal salt that is not the sulfite, bisulfite and/or metabisulfite salt of (a); and (d) optionally a sulfur-containing compound that is not the sulfite, bisulfite and/or metabisulfite salt of (a); and (ii) oxidatively dehydrogenating the saturated hydrocarbon feed under suitable reaction conditions to produce the dehydrogenated hydrocarbon product and the water, wherein at least a portion of the oxygen transfer agent is converted to a reduced form.

Yet another aspect of the invention is a composition for oxidative dehydrogenation of a saturated hydrocarbon feed and/or for OCM, the composition comprising:

(a) at least one oxygen transfer agent comprising a sulfate salt, such as a sulfate salt of an alkali or alkaline earth metal;

(b) one or more elements selected from Groups 3 to 14 of the periodic table;

(c) optionally an alkali or alkaline earth metal salt that is not the sulfate salt of (a); and (d) optionally a sulfur-containing compound that is not the sulfate salt of (a).

Another aspect of the invention is a composition for oxidative dehydrogenation of a saturated hydrocarbon feed and/or for OCM, the composition comprising:

(a) at least one oxygen transfer agent comprising $SO_3$;

(b) one or more elements selected from Groups 3 to 14 of the periodic table;

(c) optionally an alkali or alkaline earth metal salt; and (d) optionally a sulfur-containing compound that is not $SO_3$.

Another aspect of the invention is a composition for oxidative dehydrogenation of a saturated hydrocarbon feed and/or for OCM, the composition comprising:

(a) at least one oxygen transfer agent comprising a sulfite, bisulfite and/or metabisulfite salt, such as a sulfite, bisulfite and/or metabisulfite salt of an alkali or alkaline earth metal;
(b) one or more elements selected from Groups 3 to 14 of the periodic table;
(c) optionally an alkali or alkaline earth metal salt that is not the sulfite, bisulfite and/or metabisulfite salt of (a); and
(d) optionally a sulfur-containing compound that is not the sulfite, bisulfite and/or metabisulfite salt of (a).

BRIEF DESCRIPTION OF THE DRAWINGS

The drawings are intended to illustrate specific embodiments of the invention and are not intended to otherwise limit the scope of the invention as described.

DETAILED DESCRIPTION

Figure 1:
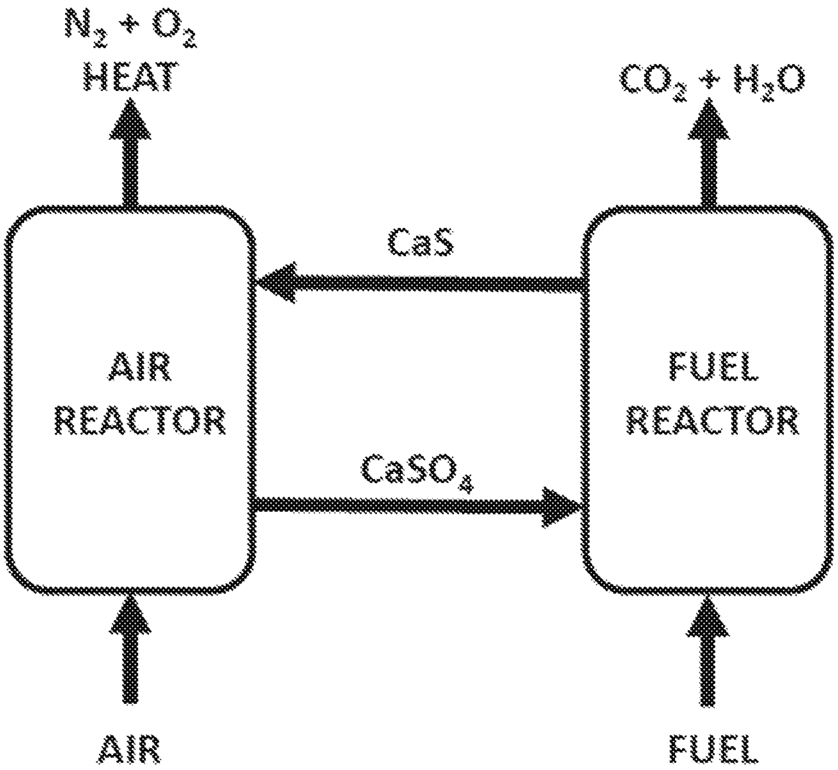
FIG. 1 shows a generalized conventional reactor system for implementing both OCM and ODH of ethane and higher hydrocarbons using redox cyclic mode or chemical looping techniques. More specifically, calcium sulfate ($CaSO_4$) acts as an OTA in the conversion of a saturated hydrocarbon feedstock (fuel) under ODH reaction conditions to the unsaturated hydrocarbon product and the $CO_2$ and $H_2O$ by-products. The oxygen-depleted OTA in the form of calcium sulfide (CaS) is then sent to a regeneration air reactor where the CaS is regenerated to $CaSO_4$ and then fed back to the fuel reactor. Although not depicted, other sulfate salts, such as a sulfate salt of an alkali or alkaline earth metal, can be substituted for $CaSO_4$ as a suitable OTA in the conversion of a saturated hydrocarbon feedstock (fuel) under ODH conditions to the unsaturated hydrocarbon product. Although not depicted, sulfur trioxide ($SO_3$) can also be substituted for $CaSO_4$ as a suitable OTA in the conversion of a saturated hydrocarbon feedstock (fuel) under ODH conditions to the unsaturated hydrocarbon product. The oxygen-depleted form of the $SO_3$ would be a reduced product in the form of, for example, $SO_2$, $H_2S$ and/or sulfur (S) which is subsequently regenerated in the air reactor back to $SO_3$ which is then fed back to the fuel reactor for further reaction. Although not depicted, a sulfite, bisulfite and/or metabisulfite salt, such as a sulfite, bisulfite and/or metabisulfite salt of an alkali or alkaline earth metal, can also be substituted for $CaSO_4$ as suitable OTAs in the conversion of a saturated hydrocarbon feedstock (fuel) under ODH conditions to the unsaturated hydrocarbon product.
Figure 2:
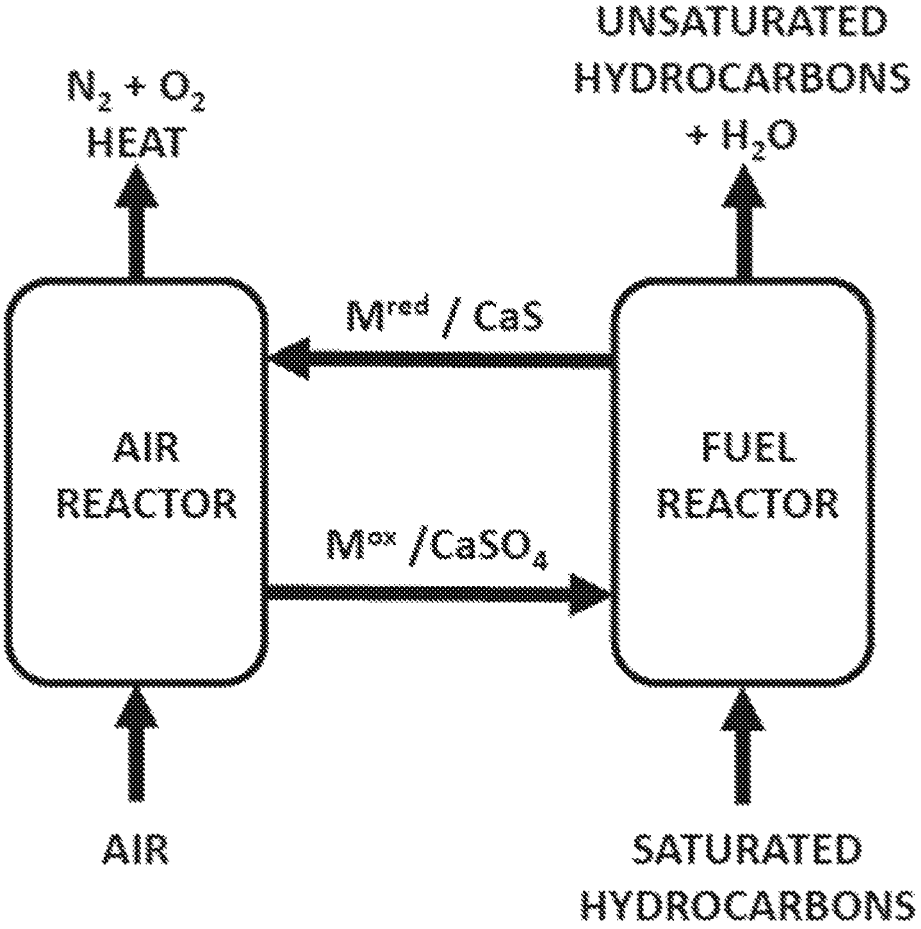
FIG. 2 shows a generalized conventional reactor system similar to that of FIG. 1 but where an element selected from Group 3 to 14 of the periodic table is used in combination with $CaSO_4$ in the conversion of a saturated hydrocarbon feedstock under ODH reaction conditions to the unsaturated hydrocarbon product. In an improvement over the use of $CaSO_4$ alone as an OTA, the amount of undesired COX by-product is minimized and the amount of $H_2O$ by-product is maximized. The Group 3 to 14 element, which is in a reduced form after the conversion, is regenerated in an air reactor along with the CaS to its original oxidized form, after which it is fed back to the fuel reactor for further reaction. Similarly to FIG. 1, other sulfate salts, $SO_3$ and sulfite, bisulfite and metabisulfite salts can also be substituted for $CaSO_4$ as suitable OTAs in the conversion of a saturated hydrocarbon feedstock (fuel) under ODH conditions to the unsaturated hydrocarbon product.

The present invention includes a method of oxidatively dehydrogenating a saturated hydrocarbon feed to produce a dehydrogenated hydrocarbon product and water, the method comprising:

contacting the saturated hydrocarbon feed at the same or different times with (a) at least one oxygen transfer agent (OTA) comprising a sulfur oxide;

(b) one or more elements selected from Groups 3 to 14 of the periodic table, (c) optionally an alkali or alkaline earth metal salt that is not the sulfur oxide of (a), and (d) optionally a sulfur-containing compound that is not the sulfur oxide of (a);

and oxidatively dehydrogenating the hydrocarbon feed under suitable reaction conditions to produce the dehydrogenated hydrocarbon product and the water.

The combination of components (a) and (b), optionally in combination with one or more of components (c) and (d), was observed to unexpectedly contribute to a high rate of conversion of the saturated hydrocarbon feed to the unsaturated hydrocarbon product while exhibiting high selectivity. Each of the components is low in cost and the OTA has a viable high temperature particle flow and fluidization in combination with low attrition. Based on these attributes, the described method satisfies the requirements for commercial viability. Each of the components (a), (b), (c) and (d) is described in more detail below.

(1) Sulfate Salts, Sulfite Salts, Bisulfite Salts, Metabisulfite Salts and Sulfur Trioxide as Sulfur Oxide Oxygen Transfer Agents The inventor has discovered that sulfur oxides such as sulfate salts ($SO_4^{2-}$), sulfite salts ($SO_3^{2-}$), bisulfite salts ($HSO_3^-$), metabisulfite salts ($S_2O_5^{2-}$) and sulfur trioxide ($SO_3$) unexpectedly perform as effective OTAs in ODH reactions with saturated hydrocarbons to produce unsaturated hydrocarbons as depicted in reaction (3) discussed herein and satisfy the requirements for commercial viability.

In an exemplary embodiment, the sulfate salts, sulfite salts, bisulfite salts and metabisulfite salts are in the form of alkali or alkaline earth sulfate salts, sulfite salts, bisulfite salts and metabisulfite salts. In a particular embodiment, the sulfate salts are selected from the group consisting of sodium sulfate, potassium sulfate, magnesium sulfate, calcium sulfate and barium sulfate; the sulfite salts are selected from the group consisting of sodium sulfite, potassium sulfite, magnesium sulfite, calcium sulfite and barium sulfite; and the bisulfite salts are selected from the group consisting of sodium bisulfite, potassium bisulfite, magnesium bisulfite, calcium bisulfite and barium bisulfite. In another particular embodiment, the sulfate salt is calcium sulfate, the sulfite salt is calcium sulfite, the bisulfite salt is calcium bisulfite, and the metabisulfite salt is calcium metabisulfite. In yet another particular embodiment, the sulfate salt is manganese sulfate, the sulfite salt is manganese sulfite, the bisulfite salt is manganese bisulfite, and the metabisulfite salt is manganese metabisulfite.

Calcium sulfate ($CaSO_4$) has been found to be an effective oxygen carrier in the field of clean coal combustion via chemical looping reactors (Q. Guo et al., Chem. Eng. Comm. 199:11, 1463-1491 (2012)) and acts as an oxygen transfer agent for the combustion of coal and natural gas at temperatures in excess of 1,000° C. Compared to other commonly used metal oxides for chemical looping combustion, $CaSO_4$ has a high oxygen-carrying capacity as shown in Table 1.

TABLE 1

Table 1. Oxygen carrying capacity of common chemical looping OTAs

| OTA | $Fe_2O_3$ | NiO | CuO | $Mn_3O_4$ | CoO | $CaSO_4$ |
|---|---|---|---|---|---|---|
| Weight % Oxygen | 30 | 21 | 20 | 20 | 21 | 47 |

This oxygen-carrying capacity of calcium sulfate is effective in lowering the reactor circulation rate which benefits the overall operations and cost of the reactor system. While $CaSO_4$ is used for the total combustion of hydrocarbons, until the present invention, there has been no demonstration reported in the conventional art of the use of $CaSO_4$ as an OTA for the selective oxidation of saturated hydrocarbons as shown in reaction (3).

The OTA is present in an amount of 10 to 90%, such as 10 to 85%, such as 10 to 75%, such as 10 to 60% by weight relative to the total weight of the components (a), (b) and (c).

(2) Elements from Groups 3 to 14 of the Periodic Table

The performance of sulfate salts, sulfite salts, bisulfite salts, metabisulfite salts and $SO_3$ as OTAs for the selective oxidation of saturated hydrocarbons (such as in OCM and ODH reactions) was observed to be enhanced by the presence of one or more elements (typically in salt form) selected from Groups 3 to 14 of the periodic table. In an exemplary embodiment, the element is selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the element is iron (Fe). In another particular embodiment, the element is Fe in combination with another element from Groups 3 to 14 of the periodic table.

In an exemplary embodiment, the enhanced OTA composition comprises a sulfate salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition comprises an alkali or an alkaline earth sulfate salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition comprises $CaSO_4$ and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition comprises a sulfate salt and a Fe salt. In a particular embodiment, the enhanced OTA composition comprises a sulfate salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition comprises an alkali or alkaline earth sulfate salt and a Fe salt. In a particular embodiment, the enhanced OTA composition comprises an alkali or alkaline earth sulfate salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition comprises $CaSO_4$ and a Fe salt. In a particular embodiment, the enhanced OTA composition comprises $CaSO_4$, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In an exemplary embodiment, the Fe salt is selected from the group consisting of iron chloride, iron bromide, iron sulfate, iron nitrate, iron citrate and iron phosphate. Suitable Fe salts include both ferric ($^{3+}$) and ferrous ($^{2+}$) oxidation states.

In an exemplary embodiment, the enhanced OTA composition consists essentially of a sulfate salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition consists essentially of an alkali or an alkaline earth sulfate salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists essentially of $CaSO_4$ and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists essentially of a sulfate salt and a Fe salt. In a particular embodiment, the enhanced OTA composition consists essentially of a sulfate salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists essentially of an alkali or alkaline earth sulfate salt and a Fe salt. In a particular embodiment, the enhanced OTA composition consists essentially of an alkali or alkaline earth sulfate salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists essentially of $CaSO_4$ and a Fe salt. In a particular embodiment, the enhanced OTA composition consists essentially of $CaSO_4$, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

In an exemplary embodiment, the enhanced OTA composition consists of a sulfate salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition consists of an alkali or an alkaline earth sulfate salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists of $CaSO_4$ and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists of a sulfate salt and a Fe salt. In a particular embodiment, the enhanced OTA composition consists of a sulfate salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists of an alkali or alkaline earth sulfate salt and a Fe salt. In a particular embodiment, the enhanced OTA composition consists of an alkali or alkaline earth sulfate salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists of $CaSO_4$ and a Fe salt. In a particular embodiment, the enhanced OTA composition consists of $CaSO_4$, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

In an exemplary embodiment, the enhanced OTA composition comprises a sulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition comprises an alkali or an alkaline earth sulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition comprises calcium sulfite ($CaSO_3$) and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition comprises a sulfite salt and a Fe salt. In a particular embodiment, the enhanced OTA composition comprises a sulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition comprises an alkali or alkaline earth sulfite salt and a Fe salt. In a particular embodiment, the enhanced OTA composition comprises an alkali or alkaline earth sulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition comprises calcium sulfite ($CaSO_3$) and a Fe salt. In a particular embodiment, the enhanced OTA composition comprises calcium sulfite ($CaSO_3$), a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In an exemplary embodiment, the Fe salt is selected from the group consisting of iron chloride, iron bromide, iron sulfate, iron nitrate, iron citrate and iron phosphate.

In an exemplary embodiment, the enhanced OTA composition consists essentially of a sulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition consists essentially of an alkali or an alkaline earth sulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists essentially of calcium sulfite ($CaSO_3$) and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists essentially of a sulfite salt and a Fe salt. In a particular embodiment, the enhanced OTA composition consists essentially of a sulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists essentially of an alkali or alkaline earth sulfite salt and a Fe salt. In a particular embodiment, the enhanced OTA composition consists essentially of an alkali or alkaline earth sulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists essentially of calcium sulfite ($CaSO_3$) and a Fe salt. In a particular embodiment, the enhanced OTA composition consists essentially of calcium sulfite ($CaSO_3$), a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

In an exemplary embodiment, the enhanced OTA composition consists of a sulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition consists of an alkali or an alkaline earth sulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists of calcium sulfite ($CaSO_3$) and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists of a sulfite salt and a Fe salt. In a particular embodiment, the enhanced OTA composition consists of a sulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists of an alkali or alkaline earth sulfite salt and a Fe salt. In a particular embodiment, the enhanced OTA composition consists of an alkali or alkaline earth sulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists of calcium sulfite ($CaSO_3$) and a Fe salt. In a particular embodiment, the enhanced OTA composition consists of calcium sulfite ($CaSO_3$), a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

In an exemplary embodiment, the enhanced OTA composition comprises a bisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition comprises an alkali or an alkaline earth bisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition comprises calcium bisulfite ($CaS_2O_6H_2$) and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition comprises a bisulfite salt and a Fe salt. In a particular embodiment, the enhanced OTA composition comprises a bisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition comprises an alkali or alkaline earth bisulfite salt and a Fe salt. In a particular embodiment, the enhanced OTA composition comprises an alkali or alkaline earth bisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition comprises calcium bisulfite ($CaS_2O_6H_2$) and a Fe salt. In a particular embodiment, the enhanced OTA composition comprises calcium bisulfite ($CaS_2O_6H_2$), a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In an exemplary embodiment, the Fe salt is selected from the group consisting of iron chloride, iron bromide, iron sulfate, iron nitrate, iron citrate and iron phosphate.

In an exemplary embodiment, the enhanced OTA composition consists essentially of a bisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition consists essentially of an alkali or an alkaline earth bisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists essentially of calcium bisulfite ($CaS_2O_6H_2$) and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists essentially of a bisulfite salt and a Fe salt. In a particular embodiment, the enhanced OTA composition consists essentially of a bisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists essentially of an alkali or alkaline earth bisulfite salt and a Fe salt. In a particular embodiment, the enhanced OTA composition consists essentially of an alkali or alkaline earth bisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists essentially of calcium bisulfite ($CaS_2O_6H_2$) and a Fe salt. In a particular embodiment, the enhanced OTA composition consists essentially of calcium bisulfite ($CaS_2O_6H_2$), a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

In an exemplary embodiment, the enhanced OTA composition consists of a bisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition consists of an alkali or an alkaline earth bisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists of calcium bisulfite ($CaS_2O_6H_2$) and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists of a bisulfite salt and a Fe salt. In a particular embodiment, the enhanced OTA composition consists of a bisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists of an alkali or alkaline earth bisulfite salt and a Fe salt. In a particular embodiment, the enhanced OTA composition consists of an alkali or alkaline earth bisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists of calcium bisulfite ($CaS_2O_6H_2$) and a Fe salt. In a particular embodiment, the enhanced OTA composition consists of calcium bisulfite ($CaS_2O_6H_2$), a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

In an exemplary embodiment, the enhanced OTA composition comprises a metabisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition comprises an alkali or an alkaline earth metabisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition comprises calcium metabisulfite ($CaS_2O_5$) and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition comprises a metabisulfite salt and a Fe salt. In a particular embodiment, the enhanced OTA composition comprises a metabisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition comprises an alkali or alkaline earth metabisulfite salt and a Fe salt. In a particular embodiment, the enhanced OTA composition comprises an alkali or alkaline earth metabisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition comprises calcium metabisulfite ($CaS_2O_5$) and a Fe salt. In a particular embodiment, the enhanced OTA composition comprises calcium metabisulfite ($CaS_2O_5$), a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In an exemplary embodiment, the Fe salt is selected from the group consisting of iron chloride, iron bromide, iron sulfate, iron nitrate, iron citrate and iron phosphate.

In an exemplary embodiment, the enhanced OTA composition consists essentially of a metabisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition consists essentially of an alkali or an alkaline earth metabisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists essentially of calcium metabisulfite ($CaS_2O_5$) and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists essentially of a metabisulfite salt and a Fe salt. In a particular embodiment, the enhanced OTA composition consists essentially of a metabisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists essentially of an alkali or alkaline earth metabisulfite salt and a Fe salt. In a particular embodiment, the enhanced OTA composition consists essentially of an alkali or alkaline earth metabisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists essentially of calcium metabisulfite ($CaS_2O_5$) and a Fe salt. In a particular embodiment, the enhanced OTA composition consists essentially of calcium metabisulfite ($CaS_2O_5$), a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

In an exemplary embodiment, the enhanced OTA composition consists of a metabisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In an exemplary embodiment, the enhanced OTA composition consists of an alkali or an alkaline earth metabisulfite salt and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists of calcium metabisulfite ($CaS_2O_5$) and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists of a metabisulfite salt and a Fe salt. In a particular embodiment, the enhanced OTA composition consists of a metabisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists of an alkali or alkaline earth metabisulfite salt and a Fe salt. In a particular embodiment, the enhanced OTA composition consists of an alkali or alkaline earth metabisulfite salt, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof. In a particular embodiment, the enhanced OTA composition consists of calcium metabisulfite ($CaS_2O_5$) and a Fe salt. In a particular embodiment, the enhanced OTA composition consists of calcium metabisulfite ($CaS_2O_5$), a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

In an exemplary embodiment, the enhanced OTA composition comprises $SO_3$ and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition comprises $SO_3$ and a Fe salt. In a particular embodiment, the enhanced OTA composition comprises $SO_3$, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

In an exemplary embodiment, the enhanced OTA composition consists essentially of $SO_3$ and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists essentially of $SO_3$ and a Fe salt. In a particular embodiment, the enhanced OTA composition consists essentially of a $SO_3$, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

In an exemplary embodiment, the enhanced OTA composition consists of $SO_3$ and a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof. In a particular embodiment, the enhanced OTA composition consists of $SO_3$ and a Fe salt. In a particular embodiment, the enhanced OTA composition consists of $SO_3$, a Fe salt and a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof.

The one or more elements from Groups 3 to 14 of the periodic table are present in an amount of 0.10 to 90%, such as 1 to 85%, such as 5 to 75%, such as 10 to 70%, such as 10 to 65%, such as 10 to 60%, such as 10 to 60% by weight relative to the total weight of the components (a), (b) and (c).

(3) Alkali or Alkaline Earth Salts

The performance of sulfate salts, sulfite salts, bisulfite salts, metabisulfite salts and $SO_3$ as OTAs for the selective oxidation of saturated hydrocarbons (such as in OCM and ODH reactions) was observed to frequently be enhanced by the presence of one or more alkali or alkaline earth metals. In an exemplary embodiment, the alkali metal is selected from the group consisting of Li, Na, K and combinations thereof, and the alkaline earth metal is selected from the group consisting of Mg, Ca, Ba and combinations thereof. In a particular embodiment, the OTA is an alkaline earth sulfate salt and the enhancing alkali or alkaline earth salt is an alkali salt. In a particular embodiment, the OTA is an alkaline earth sulfite salt and the enhancing alkali or alkaline earth salt is an alkali salt. In a particular embodiment, the OTA is an alkaline earth bisulfite salt and the enhancing alkali or alkaline earth salt is an alkali salt. In a particular embodiment, the OTA is an alkaline earth metabisulfite salt and the enhancing alkali or alkaline earth salt is an alkali salt.

In an exemplary embodiment, the enhanced OTA composition comprises a sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the sulfate salt. In an exemplary embodiment, the enhanced OTA composition comprises an alkali or an alkaline earth sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth sulfate salt. In a particular embodiment, the enhanced OTA composition comprises $CaSO_4$; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not $CaSO_4$. In a particular embodiment, the enhanced OTA composition comprises a sulfate salt; a Fe salt; and an alkali or alkaline earth metal salt that is not the sulfate salt. In a particular embodiment, the enhanced OTA composition comprises a sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the sulfate salt. In a particular embodiment, the enhanced OTA composition comprises an alkali or alkaline earth sulfate salt; a Fe salt; and an alkali or alkaline earth metal salt that is not the alkali or alkaline earth sulfate salt. In a particular embodiment, the enhanced OTA composition comprises an alkali or alkaline earth sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth sulfate salt. In a particular embodiment, the enhanced OTA composition comprises $CaSO_4$; a Fe salt; and an alkali or alkaline earth metal salt that is not $CaSO_4$. In a particular embodiment, the enhanced OTA composition comprises $CaSO_4$; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not $CaSO_4$.

In an exemplary embodiment, the enhanced OTA composition consists essentially of a sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the sulfate salt. In an exemplary embodiment, the enhanced OTA composition consists essentially of an alkali or an alkaline earth sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth sulfate salt. In a particular embodiment, the enhanced OTA composition consists essentially of $CaSO_4$; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not $CaSO_4$. In a particular embodiment, the enhanced OTA composition consists essentially of a sulfate salt; a Fe salt; and an alkali or alkaline earth metal salt that is not the sulfate salt. In a particular embodiment, the enhanced OTA composition consists essentially of a sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the sulfate salt. In a particular embodiment, the enhanced OTA composition consists essentially of an alkali or alkaline earth sulfate salt; a Fe salt; and an alkali or alkaline earth metal salt that is not the alkali or alkaline earth sulfate salt. In a particular embodiment, the enhanced OTA composition consists essentially of an alkali or alkaline earth sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth sulfate salt. In a particular embodiment, the enhanced OTA composition consists essentially of $CaSO_4$; a Fe salt; and an alkali or alkaline earth metal salt that is not $CaSO_4$. In a particular embodiment, the enhanced OTA composition consists essentially of $CaSO_4$; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not $CaSO_4$.

In an exemplary embodiment, the enhanced OTA composition consists of a sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the sulfate salt. In an exemplary embodiment, the enhanced OTA composition consists of an alkali or an alkaline earth sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth metal sulfate salt. In a particular embodiment, the enhanced OTA composition consists of $CaSO_4$; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not $CaSO_4$. In a particular embodiment, the enhanced OTA composition consists of a sulfate salt; a Fe salt; and an alkali or alkaline earth metal salt that is not the sulfate salt. In a particular embodiment, the enhanced OTA composition consists of a sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the sulfate salt. In a particular embodiment, the enhanced OTA composition consists of an alkali or alkaline earth sulfate salt; a Fe salt; and an alkali or alkaline earth metal salt that is not the alkali or alkaline earth metal sulfate salt. In a particular embodiment, the enhanced OTA composition consists of an alkali or alkaline earth sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth metal sulfate salt. In a particular embodiment, the enhanced OTA composition consists of $CaSO_4$; a Fe salt; and an alkali or alkaline earth metal salt that is not $CaSO_4$. In a particular embodiment, the enhanced OTA composition consists of $CaSO_4$; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not $CaSO_4$.

In an exemplary embodiment, the enhanced OTA composition comprises a sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the sulfite salt. In an exemplary embodiment, the enhanced OTA composition comprises an alkali or an alkaline earth sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth sulfite salt. In a particular embodiment, the enhanced OTA composition comprises calcium sulfite ($CaSO_3$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not calcium sulfite ($CaSO_3$). In a particular embodiment, the enhanced OTA composition comprises a sulfite salt; a Fe salt; and an alkali or alkaline earth metal salt that is not the sulfite salt. In a particular embodiment, the enhanced OTA composition comprises a sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the sulfite salt. In a particular embodiment, the enhanced OTA composition comprises an alkali or alkaline earth sulfite salt; a Fe salt; and an alkali or alkaline earth metal salt that is not the alkali or alkaline earth sulfite salt. In a particular embodiment, the enhanced OTA composition comprises an alkali or alkaline earth sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth sulfite salt. In a particular embodiment, the enhanced OTA composition comprises calcium sulfite ($CaSO_3$); a Fe salt; and an alkali or alkaline earth metal salt that is not calcium sulfite ($CaSO_3$). In a particular embodiment, the enhanced OTA composition comprises calcium sulfite ($CaSO_3$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not calcium sulfite ($CaSO_3$).

In an exemplary embodiment, the enhanced OTA composition consists essentially of a sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the sulfite salt. In an exemplary embodiment, the enhanced OTA composition consists essentially of an alkali or an alkaline earth sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth sulfite salt. In a particular embodiment, the enhanced OTA composition consists essentially of calcium sulfite ($CaSO_3$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not calcium sulfite ($CaSO_3$). In a particular embodiment, the enhanced OTA composition consists essentially of a sulfite salt; a Fe salt; and an alkali or alkaline earth metal salt that is not the sulfite salt. In a particular embodiment, the enhanced OTA composition consists essentially of a sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the sulfite salt. In a particular embodiment, the enhanced OTA composition consists essentially of an alkali or alkaline earth sulfite salt; a Fe salt; and an alkali or alkaline earth metal salt that is not the alkali or alkaline earth sulfite salt. In a particular embodiment, the enhanced OTA composition consists essentially of an alkali or alkaline earth sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth sulfite salt. In a particular embodiment, the enhanced OTA composition consists essentially of calcium sulfite ($CaSO_3$); a Fe salt; and an alkali or alkaline earth metal salt that is not calcium sulfite ($CaSO_3$). In a particular embodiment, the enhanced OTA composition consists essentially of calcium sulfite ($CaSO_3$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not calcium sulfite ($CaSO_3$).

In an exemplary embodiment, the enhanced OTA composition consists of a sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the sulfite salt. In an exemplary embodiment, the enhanced OTA composition consists of an alkali or an alkaline earth sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth metal sulfite salt. In a particular embodiment, the enhanced OTA composition consists of calcium sulfite ($CaSO_3$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not calcium sulfite ($CaSO_3$). In a particular embodiment, the enhanced OTA composition consists of a sulfite salt; a Fe salt; and an alkali or alkaline earth metal salt that is not the sulfite salt. In a particular embodiment, the enhanced OTA composition consists of a sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the sulfite salt. In a particular embodiment, the enhanced OTA composition consists of an alkali or alkaline earth sulfite salt; a Fe salt; and an alkali or alkaline earth metal salt that is not the alkali or alkaline earth metal sulfite salt. In a particular embodiment, the enhanced OTA composition consists of an alkali or alkaline earth sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth metal sulfite salt. In a particular embodiment, the enhanced OTA composition consists of calcium sulfite ($CaSO_3$); a Fe salt; and an alkali or alkaline earth metal salt that is not calcium sulfite ($CaSO_3$). In a particular embodiment, the enhanced OTA composition consists of calcium sulfite ($CaSO_3$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not calcium sulfite ($CaSO_3$).

In an exemplary embodiment, the enhanced OTA composition comprises a bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the bisulfite salt. In an exemplary embodiment, the enhanced OTA composition comprises an alkali or an alkaline earth bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth bisulfite salt. In a particular embodiment, the enhanced OTA composition comprises calcium bisulfite ($CaS_2O_6H_2$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not calcium bisulfite ($CaS_2O_6H_2$). In a particular embodiment, the enhanced OTA composition comprises a bisulfite salt; a Fe salt; and an alkali or alkaline earth metal salt that is not the bisulfite salt. In a particular embodiment, the enhanced OTA composition comprises a bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the bisulfite salt. In a particular embodiment, the enhanced OTA composition comprises an alkali or alkaline earth bisulfite salt; a Fe salt; and an alkali or alkaline earth metal salt that is not the alkali or alkaline earth bisulfite salt. In a particular embodiment, the enhanced OTA composition comprises an alkali or alkaline earth bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth bisulfite salt. In a particular embodiment, the enhanced OTA composition comprises calcium bisulfite ($CaS_2O_6H_2$); a Fe salt; and an alkali or alkaline earth metal salt that is not calcium bisulfite ($CaS_2O_6H_2$). In a particular embodiment, the enhanced OTA composition comprises calcium bisulfite ($CaS_2O_6H_2$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not calcium bisulfite ($CaS_2O_6H_2$).

In an exemplary embodiment, the enhanced OTA composition consists essentially of a bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the bisulfite salt. In an exemplary embodiment, the enhanced OTA composition consists essentially of an alkali or an alkaline earth bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth bisulfite salt. In a particular embodiment, the enhanced OTA composition consists essentially of calcium bisulfite ($CaS_2O_6H_2$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not calcium bisulfite ($CaS_2O_6H_2$). In a particular embodiment, the enhanced OTA composition consists essentially of a bisulfite salt; a Fe salt; and an alkali or alkaline earth metal salt that is not the bisulfite salt. In a particular embodiment, the enhanced OTA composition consists essentially of a bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the bisulfite salt. In a particular embodiment, the enhanced OTA composition consists essentially of an alkali or alkaline earth bisulfite salt; a Fe salt; and an alkali or alkaline earth metal salt that is not the alkali or alkaline earth bisulfite salt. In a particular embodiment, the enhanced OTA composition consists essentially of an alkali or alkaline earth bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth bisulfite salt. In a particular embodiment, the enhanced OTA composition consists essentially of calcium bisulfite ($CaS_2O_6H_2$); a Fe salt; and an alkali or alkaline earth metal salt that is not calcium bisulfite ($CaS_2O_6H_2$). In a particular embodiment, the enhanced OTA composition consists essentially of calcium bisulfite ($CaS_2O_6H_2$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not calcium bisulfite ($CaS_2O_6H_2$).

In an exemplary embodiment, the enhanced OTA composition consists of a bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the bisulfite salt. In an exemplary embodiment, the enhanced OTA composition consists of an alkali or an alkaline earth bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth metal bisulfite salt. In a particular embodiment, the enhanced OTA composition consists of calcium bisulfite ($CaS_2O_6H_2$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not calcium bisulfite ($CaS_2O_6H_2$). In a particular embodiment, the enhanced OTA composition consists of a bisulfite salt; a Fe salt; and an alkali or alkaline earth metal salt that is not the bisulfite salt. In a particular embodiment, the enhanced OTA composition consists of a bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the bisulfite salt. In a particular embodiment, the enhanced OTA composition consists of an alkali or alkaline earth bisulfite salt; a Fe salt; and an alkali or alkaline earth metal salt that is not the alkali or alkaline earth metal bisulfite salt. In a particular embodiment, the enhanced OTA composition consists of an alkali or alkaline earth bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth metal bisulfite salt. In a particular embodiment, the enhanced OTA composition consists of calcium bisulfite ($CaS_2O_6H_2$); a Fe salt; and an alkali or alkaline earth metal salt that is not calcium bisulfite ($CaS_2O_6H_2$). In a particular embodiment, the enhanced OTA composition consists of calcium bisulfite ($CaS_2O_6H_2$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not calcium bisulfite ($CaS_2O_6H_2$).

In an exemplary embodiment, the enhanced OTA composition comprises a metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the metabisulfite salt. In an exemplary embodiment, the enhanced OTA composition comprises an alkali or an alkaline earth metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth metabisulfite salt. In a particular embodiment, the enhanced OTA composition comprises calcium metabisulfite ($CaS_2O_5$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not calcium metabisulfite ($CaS_2O_5$). In a particular embodiment, the enhanced OTA composition comprises a metabisulfite salt; a Fe salt; and an alkali or alkaline earth metal salt that is not the metabisulfite salt. In a particular embodiment, the enhanced OTA composition comprises a metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the metabisulfite salt. In a particular embodiment, the enhanced OTA composition comprises an alkali or alkaline earth metabisulfite salt; a Fe salt; and an alkali or alkaline earth metal salt that is not the alkali or alkaline earth metabisulfite salt. In a particular embodiment, the enhanced OTA composition comprises an alkali or alkaline earth metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth metabisulfite salt. In a particular embodiment, the enhanced OTA composition comprises calcium metabisulfite ($CaS_2O_5$); a Fe salt; and an alkali or alkaline earth metal salt that is not calcium metabisulfite ($CaS_2O_5$). In a particular embodiment, the enhanced OTA composition comprises calcium metabisulfite ($CaS_2O_5$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not calcium metabisulfite ($CaS_2O_5$).

In an exemplary embodiment, the enhanced OTA composition consists essentially of a metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the metabisulfite salt. In an exemplary embodiment, the enhanced OTA composition consists essentially of an alkali or an alkaline earth metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth metabisulfite salt. In a particular embodiment, the enhanced OTA composition consists essentially calcium metabisulfite ($CaS_2O_5$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not calcium metabisulfite ($CaS_2O_5$).

In a particular embodiment, the enhanced OTA composition consists essentially of a metabisulfite salt; a Fe salt; and an alkali or alkaline earth metal salt that is not the metabisulfite salt. In a particular embodiment, the enhanced OTA composition consists essentially of a metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the metabisulfite salt. In a particular embodiment, the enhanced OTA composition consists essentially of an alkali or alkaline earth metabisulfite salt; a Fe salt; and an alkali or alkaline earth metal salt that is not the alkali or alkaline earth metabisulfite salt. In a particular embodiment, the enhanced OTA composition consists essentially of an alkali or alkaline earth metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth metabisulfite salt. In a particular embodiment, the enhanced OTA composition consists essentially of calcium metabisulfite ($CaS_2O_5$); a Fe salt; and an alkali or alkaline earth metal salt that is not calcium metabisulfite ($CaS_2O_5$). In a particular embodiment, the enhanced OTA composition consists essentially of calcium metabisulfite ($CaS_2O_5$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not calcium metabisulfite ($CaS_2O_5$).

In an exemplary embodiment, the enhanced OTA composition consists of a metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the metabisulfite salt. In an exemplary embodiment, the enhanced OTA composition consists of an alkali or an alkaline earth metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt that is not the alkali or alkaline earth metal metabisulfite salt. In a particular embodiment, the enhanced OTA composition consists of calcium metabisulfite ($CaS_2O_5$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali metal salt or an alkaline earth metal salt that is not calcium metabisulfite ($CaS_2O_5$). In a particular embodiment, the enhanced OTA composition consists of a metabisulfite salt; a Fe salt; and an alkali or alkaline earth metal salt that is not the metabisulfite salt. In a particular embodiment, the enhanced OTA composition consists of a metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the metabisulfite salt. In a particular embodiment, the enhanced OTA composition consists of an alkali or alkaline earth metabisulfite salt; a Fe salt; and an alkali or alkaline earth metal salt that is not the alkali or alkaline earth metal metabisulfite salt. In a particular embodiment, the enhanced OTA composition consists of an alkali or alkaline earth metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not the alkali or alkaline earth metal metabisulfite salt. In a particular embodiment, the enhanced OTA composition consists of calcium metabisulfite ($CaS_2O_5$); a Fe salt; and an alkali or alkaline earth metal salt that is not calcium metabisulfite ($CaS_2O_5$). In a particular embodiment, the enhanced OTA composition consists of calcium metabisulfite ($CaS_2O_5$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt that is not calcium metabisulfite ($CaS_2O_5$).

In an exemplary embodiment, the enhanced OTA composition comprises $SO_3$; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt. In a particular embodiment, the enhanced OTA composition comprises $SO_3$; a Fe salt; and an alkali or alkaline earth metal salt. In a particular embodiment, the enhanced OTA composition comprises $SO_3$, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt.

In an exemplary embodiment, the enhanced OTA composition consists essentially of $SO_3$; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt. In a particular embodiment, the enhanced OTA composition consists essentially of $SO_3$; a Fe salt; and an alkali or alkaline earth metal salt. In a particular embodiment, the enhanced OTA composition consists essentially of a $SO_3$; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt.

In an exemplary embodiment, the enhanced OTA composition consists of $SO_3$; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; and an alkali or alkaline earth metal salt. In a particular embodiment, the enhanced OTA composition consists of $SO_3$; a Fe salt; and an alkali or alkaline earth metal salt. In a particular embodiment, the enhanced OTA composition consists of $SO_3$; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; and an alkali or alkaline earth metal salt.

The alkali or alkaline earth salts are present in an amount of 0.10 to 10%, such as 0.5 to 10%, such as 0.5 to 8%, such as 0.5 to 5%, such as 1 to 10%, such as 1 to 5% by weight relative to the total weight of the components (a), (b) and (c).

(4) Sulfur-Containing Compounds

The performance of sulfate salts, sulfite salts and metabisulfite salts as OTAs for the selective oxidation of saturated hydrocarbons (such as in OCM and ODH reactions) was observed to frequently be enhanced by the presence of sulfur-containing compounds, especially those that exist as gases under the reaction conditions of the ODH of saturated hydrocarbons to unsaturated hydrocarbons. In an exemplary embodiment, the sulfur-containing compound includes, but is not limited to, dimethyl sulfide, diethyl sulfide, ethylene sulfide, diamyl sulfide, diallyl sulfide, dicyclohexyl sulfide, $SO_3$, $SO_2$, $H_2S$ and $CS_2$.

In an exemplary embodiment, the enhanced OTA composition comprises a sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In an exemplary embodiment, the enhanced OTA composition comprises an alkali or an alkaline earth sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In a particular embodiment, the enhanced OTA composition comprises $CaSO_4$; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not $CaSO_4$; and a sulfur-containing compound that is not $CaSO_4$. In a particular embodiment, the enhanced OTA composition comprises a sulfate salt; a Fe salt; an alkali or alkaline earth metal salt that is not the sulfate salt; and a sulfur-containing compound that is not the sulfate salt. In a particular embodiment, the enhanced OTA composition comprises a sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In a particular embodiment, the enhanced OTA composition comprises an alkali or alkaline earth sulfate salt; a Fe salt; an alkali or alkaline earth metal salt that is not the sulfate salt; and a sulfur-containing compound that is not the sulfate salt.

In a particular embodiment, the enhanced OTA composition comprises an alkali or alkaline earth sulfate salt; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In a particular embodiment, the enhanced OTA composition comprises $CaSO_4$; a Fe salt; an alkali or alkaline earth metal salt that is not $CaSO_4$; and a sulfur-containing compound that is not $CaSO_4$. In a particular embodiment, the enhanced OTA composition comprises $CaSO_4$; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not $CaSO_4$; and a sulfur-containing compound that is not $CaSO_4$.

In an exemplary embodiment, the enhanced OTA composition consists essentially of a sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In an exemplary embodiment, the enhanced OTA composition consists essentially of an alkali or an alkaline earth sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In a particular embodiment, the enhanced OTA composition consists essentially of $CaSO_4$; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not $CaSO_4$; and a sulfur-containing compound that is not $CaSO_4$. In a particular embodiment, the enhanced OTA composition consists essentially of a sulfate salt; a Fe salt; an alkali or alkaline earth metal salt that is not the sulfate salt; and a sulfur-containing compound that is not the sulfate salt. In a particular embodiment, the enhanced OTA composition consists essentially of a sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In a particular embodiment, the enhanced OTA composition consists essentially of an alkali or alkaline earth sulfate salt; a Fe salt; an alkali or alkaline earth metal salt that is not the sulfate salt; and a sulfur-containing compound that is not the sulfate salt. In a particular embodiment, the enhanced OTA composition consists essentially of an alkali or alkaline earth sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In a particular embodiment, the enhanced OTA composition consists essentially of $CaSO_4$; a Fe salt; an alkali or alkaline earth metal salt that is not $CaSO_4$; and a sulfur-containing compound that is not $CaSO_4$. In a particular embodiment, the enhanced OTA composition consists essentially of $CaSO_4$; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not $CaSO_4$; and a sulfur-containing compound that is not $CaSO_4$.

In an exemplary embodiment, the enhanced OTA composition consists of a sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In an exemplary embodiment, the enhanced OTA composition consists of an alkali or an alkaline earth sulfate salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In a particular embodiment, the enhanced OTA composition consists of $CaSO_4$; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not $CaSO_4$; and a sulfur-containing compound that is not $CaSO_4$. In a particular embodiment, the enhanced OTA composition consists of a sulfate salt; a Fe salt; and an alkali or alkaline earth metal salt that is not the sulfate salt. In a particular embodiment, the enhanced OTA composition consists of a sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In a particular embodiment, the enhanced OTA composition consists of an alkali or alkaline earth sulfate salt; a Fe salt; an alkali or alkaline earth metal salt that is not the sulfate salt; and a sulfur-containing compound that is not the sulfate salt. In a particular embodiment, the enhanced OTA composition consists of an alkali or alkaline earth sulfate salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfate salt; and a sulfur-containing compound that is not the sulfate salt. In a particular embodiment, the enhanced OTA composition consists of $CaSO_4$; a Fe salt; an alkali or alkaline earth metal salt that is not $CaSO_4$; and a sulfur-containing compound that is not $CaSO_4$. In a particular embodiment, the enhanced OTA composition consists of $CaSO_4$; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not $CaSO_4$; and a sulfur-containing compound that is not $CaSO_4$.

In an exemplary embodiment, the enhanced OTA composition comprises a sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In an exemplary embodiment, the enhanced OTA composition comprises an alkali or an alkaline earth sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In a particular embodiment, the enhanced OTA composition comprises calcium sulfite ($CaSO_3$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not calcium sulfite ($CaSO_3$); and a sulfur-containing compound that is not calcium sulfite ($CaSO_3$). In a particular embodiment, the enhanced OTA composition comprises a sulfite salt; a Fe salt; an alkali or alkaline earth metal salt that is not the sulfite salt; and a sulfur-containing compound that is not the sulfite salt. In a particular embodiment, the enhanced OTA composition comprises a sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In a particular embodiment, the enhanced OTA composition comprises an alkali or alkaline earth sulfite salt; a Fe salt; an alkali or alkaline earth metal salt that is not the sulfite salt; and a sulfur-containing compound that is not the sulfite salt. In a particular embodiment, the enhanced OTA composition comprises an alkali or alkaline earth sulfite salt; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In a particular embodiment, the enhanced OTA composition comprises calcium sulfite ($CaSO_3$); a Fe salt; an alkali or alkaline earth metal salt that is not calcium sulfite ($CaSO_3$); and a sulfur-containing compound that is not calcium sulfite ($CaSO_3$). In a particular embodiment, the enhanced OTA composition comprises calcium sulfite ($CaSO_3$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not calcium sulfite ($CaSO_3$); and a sulfur-containing compound that is not calcium sulfite ($CaSO_3$).

In an exemplary embodiment, the enhanced OTA composition consists essentially of a sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In an exemplary embodiment, the enhanced OTA composition consists essentially of an alkali or an alkaline earth sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In a particular embodiment, the enhanced OTA composition consists essentially of calcium sulfite ($CaSO_3$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not calcium sulfite ($CaSO_3$); and a sulfur-containing compound that is not calcium sulfite ($CaSO_3$). In a particular embodiment, the enhanced OTA composition consists essentially of a sulfite salt; a Fe salt; an alkali or alkaline earth metal salt that is not the sulfite salt; and a sulfur-containing compound that is not the sulfite salt. In a particular embodiment, the enhanced OTA composition consists essentially of a sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In a particular embodiment, the enhanced OTA composition consists essentially of an alkali or alkaline earth sulfite salt; a Fe salt; an alkali or alkaline earth metal salt that is not the sulfite salt; and a sulfur-containing compound that is not the sulfite salt. In a particular embodiment, the enhanced OTA composition consists essentially of an alkali or alkaline earth sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In a particular embodiment, the enhanced OTA composition consists essentially of calcium sulfite ($CaSO_3$); a Fe salt; an alkali or alkaline earth metal salt that is not calcium sulfite ($CaSO_3$); and a sulfur-containing compound that is not calcium sulfite ($CaSO_3$). In a particular embodiment, the enhanced OTA composition consists essentially of calcium sulfite ($CaSO_3$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not calcium sulfite ($CaSO_3$); and a sulfur-containing compound that is not calcium sulfite ($CaSO_3$).

In an exemplary embodiment, the enhanced OTA composition consists of a sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In an exemplary embodiment, the enhanced OTA composition consists of an alkali or an alkaline earth sulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In a particular embodiment, the enhanced OTA composition consists of calcium sulfite ($CaSO_3$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not calcium sulfite ($CaSO_3$); and a sulfur-containing compound that is not calcium sulfite ($CaSO_3$). In a particular embodiment, the enhanced OTA composition consists of a sulfite salt; a Fe salt; and an alkali or alkaline earth metal salt that is not the sulfite salt. In a particular embodiment, the enhanced OTA composition consists of a sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In a particular embodiment, the enhanced OTA composition consists of an alkali or alkaline earth sulfite salt; a Fe salt; an alkali or alkaline earth metal salt that is not the sulfite salt; and a sulfur-containing compound that is not the sulfite salt. In a particular embodiment, the enhanced OTA composition consists of an alkali or alkaline earth sulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the sulfite salt; and a sulfur-containing compound that is not the sulfite salt. In a particular embodiment, the enhanced OTA composition consists of calcium sulfite ($CaSO_3$); a Fe salt; an alkali or alkaline earth metal salt that is not calcium sulfite ($CaSO_3$); and a sulfur-containing compound that is not calcium sulfite ($CaSO_3$). In a particular embodiment, the enhanced OTA composition consists of calcium sulfite ($CaSO_3$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not calcium sulfite ($CaSO_3$); and a sulfur-containing compound that is not calcium sulfite ($CaSO_3$).

In an exemplary embodiment, the enhanced OTA composition comprises a bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In an exemplary embodiment, the enhanced OTA composition comprises an alkali or an alkaline earth bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In a particular embodiment, the enhanced OTA composition comprises calcium bisulfite ($CaS_2O_6H_2$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not calcium bisulfite ($CaS_2O_6H_2$); and a sulfur-containing compound that is not calcium bisulfite ($CaS_2O_6H_2$). In a particular embodiment, the enhanced OTA composition comprises a bisulfite salt; a Fe salt; an alkali or alkaline earth metal salt that is not the bisulfite salt; and a sulfur-containing compound that is not the bisulfite salt. In a particular embodiment, the enhanced OTA composition comprises a bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In a particular embodiment, the enhanced OTA composition comprises an alkali or alkaline earth bisulfite salt; a Fe salt; an alkali or alkaline earth metal salt that is not the bisulfite salt; and a sulfur-containing compound that is not the bisulfite salt. In a particular embodiment, the enhanced OTA composition comprises an alkali or alkaline earth bisulfite salt; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In a particular embodiment, the enhanced OTA composition comprises calcium bisulfite ($CaS_2O_6H_2$); a Fe salt; an alkali or alkaline earth metal salt that is not calcium bisulfite ($CaS_2O_6H_2$); and a sulfur-containing compound that is not calcium bisulfite ($CaS_2O_6H_2$). In a particular embodiment, the enhanced OTA composition comprises calcium bisulfite ($CaS_2O_6H_2$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not calcium bisulfite ($CaS_2O_6H_2$); and a sulfur-containing compound that is not calcium bisulfite ($CaS_2O_6H_2$).

In an exemplary embodiment, the enhanced OTA composition consists essentially of a bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In an exemplary embodiment, the enhanced OTA composition consists essentially of an alkali or an alkaline earth bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In a particular embodiment, the enhanced OTA composition consists essentially of calcium bisulfite ($CaS_2O_6H_2$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not calcium bisulfite ($CaS_2O_6H_2$); and a sulfur-containing compound that is not calcium bisulfite ($CaS_2O_6H_2$). In a particular embodiment, the enhanced OTA composition consists essentially of a bisulfite salt; a Fe salt; an alkali or alkaline earth metal salt that is not the bisulfite salt; and a sulfur-containing compound that is not the bisulfite salt. In a particular embodiment, the enhanced OTA composition consists essentially of a bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In a particular embodiment, the enhanced OTA composition consists essentially of an alkali or alkaline earth bisulfite salt; a Fe salt; an alkali or alkaline earth metal salt that is not the bisulfite salt; and a sulfur-containing compound that is not the bisulfite salt. In a particular embodiment, the enhanced OTA composition consists essentially of an alkali or alkaline earth bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In a particular embodiment, the enhanced OTA composition consists essentially of calcium bisulfite ($CaS_2O_6H_2$); a Fe salt; an alkali or alkaline earth metal salt that is not calcium bisulfite ($CaS_2O_6H_2$); and a sulfur-containing compound that is not calcium bisulfite ($CaS_2O_6H_2$). In a particular embodiment, the enhanced OTA composition consists essentially of calcium bisulfite ($CaS_2O_6H_2$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not calcium bisulfite ($CaS_2O_6H_2$); and a sulfur-containing compound that is not calcium bisulfite ($CaS_2O_6H_2$).

In an exemplary embodiment, the enhanced OTA composition consists of a bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In an exemplary embodiment, the enhanced OTA composition consists of an alkali or an alkaline earth bisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In a particular embodiment, the enhanced OTA composition consists of calcium bisulfite ($CaS_2O_6H_2$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not calcium bisulfite ($CaS_2O_6H_2$); and a sulfur-containing compound that is not calcium bisulfite ($CaS_2O_6H_2$). In a particular embodiment, the enhanced OTA composition consists of a bisulfite salt; a Fe salt; and an alkali or alkaline earth metal salt that is not the bisulfite salt. In a particular embodiment, the enhanced OTA composition consists of a bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In a particular embodiment, the enhanced OTA composition consists of an alkali or alkaline earth bisulfite salt; a Fe salt; an alkali or alkaline earth metal salt that is not the bisulfite salt; and a sulfur-containing compound that is not the bisulfite salt. In a particular embodiment, the enhanced OTA composition consists of an alkali or alkaline earth bisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the bisulfite salt; and a sulfur-containing compound that is not the bisulfite salt. In a particular embodiment, the enhanced OTA composition consists of calcium bisulfite ($CaS_2O_6H_2$); a Fe salt; an alkali or alkaline earth metal salt that is not calcium bisulfite ($CaS_2O_6H_2$); and a sulfur-containing compound that is not calcium bisulfite ($CaS_2O_6H_2$). In a particular embodiment, the enhanced OTA composition consists of calcium bisulfite ($CaS_2O_6H_2$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not calcium bisulfite ($CaS_2O_6H_2$); and a sulfur-containing compound that is not calcium bisulfite ($CaS_2O_6H_2$).

In an exemplary embodiment, the enhanced OTA composition comprises a metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In an exemplary embodiment, the enhanced OTA composition comprises an alkali or an alkaline earth metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In a particular embodiment, the enhanced OTA composition comprises calcium metabisulfite ($CaS_2O_5$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not calcium metabisulfite ($CaS_2O_5$); and a sulfur-containing compound that is not calcium metabisulfite ($CaS_2O_5$). In a particular embodiment, the enhanced OTA composition comprises a metabisulfite salt; a Fe salt; an alkali or alkaline earth metal salt that is not the metabisulfite salt; and a sulfur-containing compound that is not the metabisulfite salt. In a particular embodiment, the enhanced OTA composition comprises a metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In a particular embodiment, the enhanced OTA composition comprises an alkali or alkaline earth metabisulfite salt; a Fe salt; an alkali or alkaline earth metal salt that is not the metabisulfite salt; and a sulfur-containing compound that is not the metabisulfite salt. In a particular embodiment, the enhanced OTA composition comprises an alkali or alkaline earth metabisulfite salt; a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In a particular embodiment, the enhanced OTA composition comprises calcium metabisulfite ($CaS_2O_5$); a Fe salt; an alkali or alkaline earth metal salt that is not calcium metabisulfite ($CaS_2O_5$); and a sulfur-containing compound that is not calcium metabisulfite ($CaS_2O_5$). In a particular embodiment, the enhanced OTA composition comprises calcium metabisulfite ($CaS_2O_5$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not calcium metabisulfite ($CaS_2O_5$); and a sulfur-containing compound that is not calcium metabisulfite ($CaS_2O_5$).

In an exemplary embodiment, the enhanced OTA composition consists essentially of a metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In an exemplary embodiment, the enhanced OTA composition consists essentially of an alkali or an alkaline earth metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In a particular embodiment, the enhanced OTA composition consists essentially of calcium metabisulfite ($CaS_2O_5$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not calcium metabisulfite ($CaS_2O_5$); and a sulfur-containing compound that is not calcium metabisulfite ($CaS_2O_5$). In a particular embodiment, the enhanced OTA composition consists essentially of a bisulfite salt; a Fe salt; an alkali or alkaline earth metal salt that is not the metabisulfite salt; and a sulfur-containing compound that is not the metabisulfite salt. In a particular embodiment, the enhanced OTA composition consists essentially of a metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In a particular embodiment, the enhanced OTA composition consists essentially of an alkali or alkaline earth metabisulfite salt; a Fe salt; an alkali or alkaline earth metal salt that is not the metabisulfite salt; and a sulfur-containing compound that is not the metabisulfite salt. In a particular embodiment, the enhanced OTA composition consists essentially of an alkali or alkaline earth metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In a particular embodiment, the enhanced OTA composition consists essentially of calcium metabisulfite ($CaS_2O_5$); a Fe salt; an alkali or alkaline earth metal salt that is not calcium metabisulfite ($CaS_2O_5$); and a sulfur-containing compound that is not calcium metabisulfite ($CaS_2O_5$). In a particular embodiment, the enhanced OTA composition consists essentially of calcium metabisulfite ($CaS_2O_5$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not calcium metabisulfite ($CaS_2O_5$); and a sulfur-containing compound that is not calcium metabisulfite ($CaS_2O_5$).

In an exemplary embodiment, the enhanced OTA composition consists of a metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In an exemplary embodiment, the enhanced OTA composition consists of an alkali or an alkaline earth metabisulfite salt; a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In a particular embodiment, the enhanced OTA composition consists of calcium metabisulfite ($CaS_2O_5$); a salt containing an element selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B, Al and combinations thereof; an alkali metal salt or an alkaline earth metal salt that is not calcium metabisulfite ($CaS_2O_5$); and a sulfur-containing compound that is not calcium metabisulfite ($CaS_2O_5$). In a particular embodiment, the enhanced OTA composition consists of a metabisulfite salt; a Fe salt; and an alkali or alkaline earth metal salt that is not the metabisulfite salt. In a particular embodiment, the enhanced OTA composition consists of a metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In a particular embodiment, the enhanced OTA composition consists of an alkali or alkaline earth metabisulfite salt; a Fe salt; an alkali or alkaline earth metal salt that is not the metabisulfite salt; and a sulfur-containing compound that is not the metabisulfite salt. In a particular embodiment, the enhanced OTA composition consists of an alkali or alkaline earth metabisulfite salt, a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not the metabisulfite salt; and a sulfur-containing compound that is not the metabisulfite salt. In a particular embodiment, the enhanced OTA composition consists of calcium metabisulfite ($CaS_2O_5$); a Fe salt; an alkali or alkaline earth metal salt that is not calcium metabisulfite ($CaS_2O_5$); and a sulfur-containing compound that is not calcium metabisulfite ($CaS_2O_5$). In a particular embodiment, the enhanced OTA composition consists of calcium metabisulfite ($CaS_2O_5$); a Fe salt; a salt containing an element selected from the group consisting of Sc, Y, La, Ti, Zr, V, Nb, Cr, Mo, W, Mn, Ru, Co, Rh, Ni, Pd, Pt, Cu, Zn, Sn, Pb, B, Al and combinations thereof; an alkali or alkaline earth metal salt that is not calcium metabisulfite ($CaS_2O_5$); and a sulfur-containing compound that is not calcium metabisulfite ($CaS_2O_5$).

The sulfur-containing compound is present in an amount of 1 to 100,000 ppm, such as 10 to 100,000 ppm, such as 50 to 75,000 ppm, such as 50 to 50,000 ppm, such as 100 to 75,000 ppm, such as 100 to 50,000 ppm, such as 200 to 75,000 ppm, such as 200 to 50,000 ppm by weight of the saturated hydrocarbon feed.

(5) Methods of Oxidatively Dehydrogenating a Saturated Hydrocarbon Feed to Produce an Unsaturated (Dehydrogenated) Hydrocarbon Product and Water Methods of oxidatively dehydrogenating a saturated hydrocarbon feed are well documented in the art (see, e.g., U.S. Pat. No. 10,138,182; Neil et al., Energy Technology 4: 1200-1208 (2016); Sofranko et al., Journal of Catalysis 302-310 (1987)) and are typically carried out by contacting the feed with an oxidation transfer agent and may proceed in the substantial absence of molecular oxygen or in the presence of molecular oxygen. In the former case, the oxidation transfer agent (OTA) as described herein may itself provide the necessary oxygen, and thus may be converted to a reduced form. In a separate step, this reduced form may be re-oxidized (regenerated) in the presence of molecular oxygen. In the latter case, the OTA may be acting more like a catalyst since it may not necessarily be changed after the oxidative dehydrogenation of the hydrocarbon feed is complete.

In an exemplary embodiment, a method of oxidatively dehydrogenating a saturated hydrocarbon feed to produce an unsaturated hydrocarbon product and water comprises, consists of, or consists essentially of the steps of:

1) contacting the hydrocarbon feed at the same or different times with
   (a) at least one oxygen transfer agent (OTA) comprising a sulfate salt, a sulfite salt, a bisulfite salt or a metabisulfite salt, such as a sulfate salt, a sulfite salt, a bisulfite salt or a metabisulfite salt of an alkali or alkaline earth metal;

(b) one or more elements (typically in salt form) selected from Groups 3 to 14 of the periodic table;

(c) optionally an alkali or alkaline earth metal salt that is not the sulfate, sulfite, bisulfite or metabisulfite salt of (a), and (d) optionally a sulfur-containing compound that is not the sulfate, sulfite, bisulfite or metabisulfite salt of (a);

2) oxidatively dehydrogenating the hydrocarbon feed under suitable reaction conditions to produce the unsaturated hydrocarbon product and water.

In various exemplary embodiments, the reaction conditions in step 2) comprise, consist essentially of, or consist of substantially no molecular oxygen during the oxidative dehydrogenation of the hydrocarbon feed. In these embodiments, at least a portion of the oxygen transfer agent may be reduced to produce a reduced oxygen transfer agent. Without wishing to be bound by theory, this condition results in the at least one OTA providing the oxygen that is needed for the oxidative dehydrogenation to occur. In particular, less than 5 wt %, such as less than 4 wt %, such as less than 3 wt %, such as less than 2 wt %, such as less than 1 wt %, such as less than 0.5 wt %, such as less than 1000 ppm, such as less than 500 ppm by weight of molecular oxygen with respect to the total amount of the hydrocarbon feed, the oxygen transfer agent and the molecular oxygen is present during the oxidative dehydrogenation step. Less than 1000 ppm of molecular oxygen is preferred. Non-limiting examples of sources of molecular oxygen include air or molecular oxygen-containing streams resulting from chemical processes.

In various exemplary embodiments, the reaction conditions in step 2) comprise temperatures of from 825-840° C. and at gas hourly space velocities of 2,400 to 4,800 $hr^{-1}$. Other suitable temperatures include, but are not limited to, from 300° C. to 1000° C., from 350° C. to 1000° C., from 400° C. to 1000° C., from 400° C. to 800° C. or from 500° C. to 700° C. Suitable pressures may range from sub-atmospheric to super-atmospheric with a range of from 0.1 to 100 atm. In various exemplary embodiments, the pressure range may be from 0.9 to 10 atm. Other suitable pressure ranges include, but are not limited to, from 0.9 to 1.5, from 0.5 to 2, from 0.9 to 5, from 0.9 to 7, or from 0.9 to 1.1 atm.

In various exemplary embodiments, the step 2) of oxidatively dehydrogenating the hydrocarbon feed proceeds according to the reaction (3) as described herein wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the at least one oxygen transfer agent. According to some embodiments, z=2, n=1, β=0, and δ=0. In particular this means that the reaction may comprise the oxidative coupling of methane to form ethylene. According to other embodiments, z=1, n=2, β=0, and δ=1. In particular, this means that the reaction may comprise the oxidative dehydrogenation of ethane to form ethylene. The oxidative dehydrogenation may comprise more than one reaction. Non-limiting examples of such multiple reactions may include: skeletal isomerization of olefins; oxidative dehydrogenation of methane to ethane and ethylene, and oxidative dehydrogenation of ethane to ethylene and higher olefins such as propylene and butylene.

In various exemplary embodiments, the method of oxidatively dehydrogenating a hydrocarbon feed may further comprise, consist of, or consist essentially of one or more of the steps of removing a portion of the reduced oxygen transfer agent; contacting the portion of the oxygen transfer agent with a gas comprising molecular oxygen to produce a regenerated oxygen transfer agent; and feeding the regenerated oxygen transfer agent to the step 1).

The oxygen transfer agents according to various embodiments of the present invention may be used in a chemical looping system to promote an ODH reaction via a Mars-van Krevelen-like mechanism. The effective utilization of the chemical looping mode of this invention may be performed in either fixed or circulating bed reactors. In the case of fixed bed reactors, multiple reactors may be used such that the oxidative dehydrogenation of the hydrocarbon feed and the re-oxidation of the oxygen transfer agent are occurring continuously and in parallel as the hydrocarbon feed and the source of molecular oxygen (such as air) are alternately cycled between the reactor and a regeneration unit while the re-oxidation takes place.

(6) Apparatus for Producing a Dehydrogenated Hydrocarbon Product:

In an exemplary embodiment, the fuel reactor of FIG. 1 is selected from a fluidized bed reactor, a moving bed reactor, or a shell and tube reactor. The air reactor may be constructed and arranged to receive the post-ODH reaction OTA in reduced form, optionally in combination with the reduced metal selected from Groups 3 to 14 of the periodic table, where the reduced OTA/optional reduced metal is contacted with a gas (such as air) comprising molecular oxygen to produce a regenerated OTA and optional regenerated Group 3 to 14 metal; and where the regenerated OTA/optional Group 3 to 14 metal is introduced back into the fuel reactor.

(7) Hydrocarbon Feed:

As defined herein, a saturated hydrocarbon that is suitable for oxidative dehydrogenation may be linear, branched, cyclic and contain one or more unsaturated carbon-carbon bonds (i.e., —C═C— and/or —C≡C—). An exemplary embodiment of such a compound is 1-butene ($CH_2$═$CH_2$—$CH_2$—$CH_3$) which contains an ODH-reactive saturated portion (—$CH_2$—$CH_3$) of the molecule as well as an unsaturated portion ($CH_2$═CH—). Suitable ODH hydrocarbon feeds for use in embodiments of the present invention include, but are not limited to, ethane; propane; butane; isomers of butane; butene; pentane; isomers of pentane; cyclopentane; pentene; cyclopentene; isomers of pentene; hexane; isomers of hexane; cyclohexane; hexene; isomers of hexene; cyclohexene; and mixtures thereof.

(8) Aspects of the Invention

Various aspects of the invention may be summarized as follows:

Aspect 1: A method of oxidatively dehydrogenating a saturated hydrocarbon feed to produce a dehydrogenated hydrocarbon product and water, the method comprising: contacting the saturated hydrocarbon feed at the same or different times with (a) at least one oxygen transfer agent comprising a sulfate salt, a sulfite salt, a bisulfite salt or a metabisulfite salt, such as a sulfate salt, a sulfite salt, a bisulfite salt or a metabisulfite salt of an alkali or alkaline earth metal; (b) one or more elements (typically in salt form) selected from Groups 3 to 14 of the periodic table; (c) optionally an alkali or alkaline earth metal salt that is not the sulfate, sulfite, bisulfite or metabisulfite salt of (a); and (d) optionally a sulfur-containing compound that is not the sulfate, sulfite, bisulfite or metabisulfite salt of (a); and oxidatively dehydrogenating the hydrocarbon feed to produce the dehydrogenated hydrocarbon product and the water.

Aspect 2: The method of Aspect 1, wherein (a) is at least one oxygen transfer agent comprising a sulfate salt, a sulfite salt, a bisulfite salt or a metabisulfite salt of an alkaline earth metal.

Aspect 3: The method of Aspect 1 or 2, wherein (a) is at least one oxygen transfer agent comprising a sulfate salt, a sulfite salt, a bisulfite salt or a metabisulfite salt of an alkaline earth metal; and (b) is one or more elements selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B and Al.

Aspect 4: The method of any of Aspects 1 to 3, wherein (a) is calcium sulfate ($CaSO_4$) or calcium sulfite ($CaSO_3$) or calcium bisulfite ($CaS_2O_6H_2$) or calcium metabisulfite ($CaS_2O_5$); and (b) is one or more elements selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B and Al.

Aspect 5: The method of any of Aspect 1, wherein the saturated hydrocarbon feed is contacted at the same or different times with (a) at least one oxygen transfer agent comprising a sulfate salt, a sulfite salt, a bisulfite salt or a metabisulfite salt of an alkali or alkaline earth metal; (b) one or more elements selected from Groups 3 to 14 of the periodic table; and (c) an alkali or alkaline earth metal salt that is not the sulfate, sulfite, bisulfite or metabisulfite salt of (a).

Aspect 6: The method of any of Aspect 1, wherein the saturated hydrocarbon feed is contacted at the same or different times with (a) at least one oxygen transfer agent comprising a sulfate salt, a sulfite salt, a bisulfite salt or a metabisulfite salt of an alkali or alkaline earth metal; (b) one or more elements selected from Groups 3 to 14 of the periodic table; (c) an alkali or alkaline earth metal salt that is not the sulfate, sulfite, bisulfite or metabisulfite salt of (a); and (d) a sulfur-containing compound that is not the sulfate, sulfite, bisulfite or metabisulfite salt of (a).

Aspect 7: The method of Aspect 5 or 6, wherein (a) is calcium sulfate ($CaSO_4$) or calcium sulfite ($CaSO_3$) or calcium bisulfite ($CaS_2O_6H_2$) or calcium metabisulfite ($CaS_2O_5$); and (b) is one or more elements selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B and Al.

Aspect 8: The method of Aspect 6 or 7, wherein (d) is selected from the group consisting of $H_2S$, $SO_2$, $SO_3$ and organosulfur compounds.

Aspect 9: The method of any of Aspects 1 to 8, wherein (b) is Fe and optionally one or more elements selected from the group consisting of Sc, Y, La, Ti, Zr, V, Nb, Cr, Mo, W, Mn, Ru, Co, Rh, Ni, Pd, Pt, Cu, Zn, Sn, Pb, B and Al.

Aspect 10: The method of any of Aspects 1 to 9, wherein the saturated hydrocarbon feed is contacted at the same or different times with (a) $CaSO_4$ or calcium sulfite ($CaSO_3$) or calcium bisulfite ($CaS_2O_6H_2$) or calcium metabisulfite ($CaS_2O_5$); (b) Fe and optionally one or more elements selected from the group consisting of Sc, Y, La, Ti, Zr, V, Nb, Cr, Mo, W, Mn, Ru, Co, Rh, Ni, Pd, Pt, Cu, Zn, Sn, Pb, B and Al; and (c) an alkali or alkaline earth metal salt that is not calcium sulfate ($CaSO_4$) or calcium sulfite ($CaSO_3$) or calcium bisulfite ($CaS_2O_6H_2$) or calcium metabisulfite ($CaS_2O_5$).

Aspect 11: The method of any of Aspects 1 to 10, wherein the saturated hydrocarbon feed is contacted at the same or different times with (a) calcium sulfate ($CaSO_4$) or calcium sulfite ($CaSO_3$) or calcium bisulfite ($CaS_2O_6H_2$) or calcium metabisulfite ($CaS_2O_5$); (b) Fe and optionally one or more elements selected from the group consisting of Sc, Y, La, Ti, Zr, V, Nb, Cr, Mo, W, Mn, Ru, Co, Rh, Ni, Pd, Pt, Cu, Zn, Sn, Pb, B and Al; (c) an alkali or alkaline earth metal salt that is not calcium sulfate ($CaSO_4$) or calcium sulfite ($CaSO_3$) or calcium bisulfite ($CaS_2O_6H_2$) or calcium metabisulfite ($CaS_2O_5$); and (d) a sulfur-containing compound that is not calcium sulfate ($CaSO_4$) or calcium sulfite ($CaSO_3$) or calcium bisulfite ($CaS_2O_6H_2$) or calcium metabisulfite ($CaS_2O_5$).

Aspect 12: The method of any of Aspects 1 to 11, wherein (a) is present in an amount of 10 to 90% by weight and (b) is present in an amount of 0.1 to 90% by weight relative to the total weight of (a), (b) and (c).

Aspect 13: The method of any of Aspects 1 to 12, wherein (c) is present in an amount of 0.1 to 10% by weight relative to the total weight of (a), (b) and (c).

Aspect 14: The method of any of Aspects 1 to 13, wherein (d) is present in an amount of 1 to 100,000 ppm relative to the saturated hydrocarbon feed.

Aspect 15: The method of any of Aspects 1 to 13, further comprising: removing after oxidative dehydrogenation at least a portion of the oxygen transfer agent in reduced form; contacting the reduced oxygen transfer agent with a gas comprising molecular oxygen to produce a regenerated oxygen transfer agent; and adding the regenerated oxygen transfer agent to the saturated hydrocarbon feed.

Aspect 16: A method of oxidatively dehydrogenating a saturated hydrocarbon feed to produce a dehydrogenated hydrocarbon product and water, the method comprising: contacting the saturated hydrocarbon feed at the same or different times with (a) at least one oxygen transfer agent comprising $SO_3$, (b) optionally one or more elements selected from Groups 3 to 14 of the periodic table, (c) optionally an alkali or alkaline earth metal salt, and (d) optionally a sulfur-containing compound that is not $SO_3$; and oxidatively dehydrogenating the hydrocarbon feed to produce the dehydrogenated hydrocarbon product and the water.

Aspect 17: The method of Aspect 16, wherein (a) is $SO_3$.

Aspect 18: The method of Aspect 16 or 17, wherein the saturated hydrocarbon feed is contacted at the same or different times with (a) $SO_3$ and (b) Fe and optionally one or more elements selected from the group consisting of Sc, Y, La, Ti, Zr, V, Nb, Cr, Mo, W, Mn, Ru, Co, Rh, Ni, Pd, Pt, Cu, Zn, Sn, Pb, B and Al.

Aspect 19: An apparatus configured to produce a dehydrogenated hydrocarbon product by oxidative dehydrogenation of a saturated hydrocarbon feed to produce the dehydrogenated hydrocarbon product and water, the apparatus comprising: at least one vessel configured for: (i) contacting the saturated hydrocarbon feed with (a) at least one oxygen transfer agent comprising a sulfate salt; a sulfite salt, a bisulfite salt or a metabisulfite salt of an alkali or alkaline earth metal; (b) one or more elements selected from Groups 3 to 14 of the periodic table; (c) optionally an alkali or alkaline earth metal salt that is not the sulfate, sulfite, bisulfite salt or metabisulfite salt of (a), and (d) optionally a sulfur-containing compound that is not the sulfate, sulfite, bisulfite salt or metabisulfite salt of (a); and (ii) oxidatively dehydrogenating the saturated hydrocarbon feed to produce the dehydrogenated hydrocarbon product and the water and to convert at least a portion of the oxygen transfer agent to a reduced form.

Aspect 20: An apparatus configured to produce a dehydrogenated hydrocarbon product by oxidative dehydrogenation of a saturated hydrocarbon feed to produce the dehydrogenated hydrocarbon product and water, the apparatus comprising: at least one vessel configured for: (i) contacting the saturated hydrocarbon feed with (a) at least one oxygen transfer agent comprising $SO_3$, (b) optionally one or more elements selected from Groups 3 to 14 of the periodic table, (c) optionally an alkali or alkaline earth metal salt, and (d) optionally a sulfur-containing compound that is not $SO_3$; and (ii) oxidatively dehydrogenating the saturated hydrocarbon feed to produce the dehydrogenated hydrocarbon product and the water and to convert at least a portion of the oxygen transfer agent to a reduced form.

Aspect 21: The apparatus of Aspect 19 or 20, wherein the at least one vessel is selected from a fluidized bed reactor, a moving bed reactor, a shell and tube reactor and a series of switching fixed bed reactors.

Aspect 22: The apparatus of any of Aspects 19 to 21, wherein the at least one vessel comprises an inlet and an outlet, and wherein the apparatus further comprises a regeneration unit in communication with the inlet and the outlet, wherein the regeneration unit is configured for: (iii) receiving at least a portion of the reduced oxygen transfer agent from the outlet; (iv) contacting the reduced oxygen transfer agent with a gas comprising molecular oxygen to produce a regenerated oxygen transfer agent; and (v) feeding the regenerated oxygen transfer agent to the inlet.

Aspect 23: A composition for oxidative dehydrogenation of a saturated hydrocarbon feed and for OCM, the composition comprising: (a) at least one oxygen transfer agent comprising a sulfate, sulfite, bisulfite or metabisulfite salt of an alkali or alkaline earth metal, (b) one or more elements selected from Groups 3 to 14 of the periodic table, (c) optionally an alkali or alkaline earth metal salt that is not the sulfate, sulfite, bisulfite or metabisulfite salt of (a), and (d) optionally a sulfur-containing compound that is not the sulfate, sulfite, bisulfite or metabisulfite salt of (a).

Aspect 24: A composition for oxidative dehydrogenation of a saturated hydrocarbon feed and for OCM, the composition comprising: (a) at least one oxygen transfer agent comprising $SO_3$, (b) one or more elements selected from Groups 3 to 14 of the periodic table, (c) optionally an alkali or alkaline earth metal salt, and (d) optionally a sulfur-containing compound that is not $SO_3$.

Aspect 25: The composition of Aspect 23, wherein (a) is at least one oxygen transfer agent comprising a sulfate, sulfite, bisulfite or metabisulfite salt of an alkaline earth metal.

Aspect 26: The composition of Aspect 23 or 25, wherein (a) is at least one oxygen transfer agent comprising a sulfate, sulfite, bisulfite or metabisulfite salt of an alkaline earth metal, and (b) is one or more elements selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B and Al.

Aspect 27: The composition of Aspects 23, 25 or 26, wherein (a) is calcium sulfate ($CaSO_4$) or calcium sulfite ($CaSO_3$) or calcium bisulfite ($CaS_2O_6H_2$) or calcium metabisulfite ($CaS_2O_5$), and (b) is one or more elements selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B and Al.

Aspect 28: The composition of any of Aspects 23 or 25 to 27, comprising: (c) an alkali or alkaline earth metal salt that is not a sulfate, sulfite, bisulfite or metabisulfite salt.

Aspect 29: The composition of any of Aspects 23 or 25 to 28, comprising: (d) a sulfur-containing compound that is not the sulfate, sulfite, bisulfite or metabisulfite salt of (a).

Aspect 30: The composition of Aspect 28, wherein (a) is calcium sulfate ($CaSO_4$) or calcium sulfite ($CaSO_3$) or calcium bisulfite ($CaS_2O_6H_2$) or calcium metabisulfite; and (b) is one or more elements selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B and Al.

Aspect 31: The composition of Aspect 29, wherein (a) is calcium sulfate ($CaSO_4$) or calcium sulfite ($CaSO_3$) or calcium bisulfite ($CaS_2O_6H_2$) or calcium metabisulfite; and (b) is one or more elements selected from the group consisting of Sc, Y, La, Ti, Zr, V, Nb, Cr, Mo, W, Mn, Fe, Ru, Co, Rh, Ni, Pd, Pt, Cu, Zn, Sn, Pb, B and Al.

Aspect 32: The composition of any of Aspects 23 to 31, wherein (c) is an alkali metal salt that is not the sulfate, sulfite, bisulfite or metabisulfite salt of (a).

Aspect 33: The composition of any of Aspects 23 to 32, wherein (d) is selected from the group consisting of $H_2S$, $SO_2$, $SO_3$ and organosulfur compounds.

Aspect 34: The composition of any of Aspects 23 to 33, wherein (b) is Fe and optionally one or more elements selected from the group consisting of Sc, Y, La, Ti, Zr, V, Nb, Cr, Mo, W, Mn, Ru, Co, Rh, Ni, Pd, Pt, Cu, Zn, Sn, Pb, B and Al.

EXAMPLES

The following non-limiting examples are provided for the purpose of elucidating the advantages obtained from aspects of the present invention and are not intended to limit the invention to only these exemplary embodiments.

Example 1

A two zone ½ inch ID alumina tube reactor was charged with 5.0 g of $NaHSO_4$ (sodium bisulfate) which was held at 550° C. and 5 ml of 14-30 mesh high density $\alpha$-$Al_2O_3$. It is known that $NaHSO_4$ thermally decomposes via sodium pyrosulfate at temperatures above 500° C. (K. J. de Vries et al., J. Inorg Nucl. Chem. 31, 1307-1313 (1969)). A flow of nitrogen was first passed through the $NaHSO_4$ at 550° C. and then directly through the $\alpha$-$Al_2O_3$ which was held at 800° C. The formation of $SO_3$ was confirmed by bubbling the effluent from the reactor through a water trap containing bromothymol blue. Ethane pyrolytic products were observed and 30-35% of the hydrogen formed was oxidized by the $SO_3$ to water. See Table 2.

TABLE 2

| Example # | | 1 | | 2 | | |
|---|---|---|---|---|---|---|
| OTA | | $SO_3$ | $SO_3$ | $CaSO_4$ | $CaSO_4$ | Drierite |
| Feed | | $C_2H_6$ | $C_2H_6$ | $CH_4$ | $C_2H_6$ | $C_2H_6$ |
| Temp, C. | | 800 | 800 | 1000 | 840 | 825 |
| GHSV, $hr^1$ | | 3,000 | 6,000 | 2,400 | 2,400 | 2,400 |
| % Conversion | $CH_2$ or $C_2H_6$ | 84.04% | 70.62% | 19.55% | 79.96% | 67.45% |
| % Selectivity | Olefins | 81.49% | 89.01% | 27.77% | 86.09% | 93.31% |
| % Yield | Olefins | 68.49% | 62.86% | 5.43% | 68.84% | 62.94% |
| % Selectivity | Carbon Dioxide | 2.62% | 1.33% | 39.40% | 0.76% | 0.41% |
| % Selectivity | Carbon Monoxide | 4.37% | 2.3% | 32.83% | 0.48% | 0.56% |
| % Yield | Carbon Dioxide | 2.20% | 0.94% | 7.70% | 0.61% | 0.28% |
| % Yield | Carbon Monoxide | 3.67% | 1.67% | 6.42% | 0.38% | 0.37% |
| % Selectivity | % $H_2$ Selectivity | 70.07% | 64.70% | 10.88% | 61.06% | 82.51% |
| % Selectivity | % $H_2O$ Selectivity | 29.93% | 35.30% | 89.12% | 38.94% | 17.49% |

Example 2

A ½ inch ID alumina tube reactor was charged with either anhydrous $CaSO_4$ or commercial purchased Drierite. Ethane was passed through the bed at the conditions shown in Table 2 and products analyzed by GC. Both methane and ethane were converted to olefins with up to 89% of the hydrogen formed converted to water, which indicates the ability of $CaSO_4$ to act as an oxygen carrier OTA for OCM and ODH.

Example 3

A series of OTAs were prepared by dry mixing mixtures of iron or manganese compounds with $CaSO_4$. The mixtures were made up to be 5% by weight of the metal compound. Sodium promoters were optionally added at a 1:1 mole ratio to the metal. Ammonium metatungstate (AMT) and platinum were optionally separately added as promoters. After thoroughly mixing of the dry reagents, distilled water was added to generate a paste. The resultant paste was dried at 110° C. overnight, and then calcined at 900° C. in air for 16 hours. The catalyst cake was broken down to 14-30 mesh particles and charged to an alumina reactor for OCM and ODH testing. A summary of these materials and run results is shown in Tables 3-4.

TABLE 3

| OTA Composition | | $MnSO_4$/CaSO4 | | $FeSO_4/CaSO_4$ | | |
|---|---|---|---|---|---|---|
| Feed | | $CH_4$ | $C_2H_6$ | $CH_4$ | $C_2H_6$ | $C_2H_6$ |
| Temp, C. | | 825 | 840 | 825 | 825 | 840 |
| GHSV, hr[1] | | 1,200 | 2,400 | 2,400 | 2,400 | 2,400 |
| % Conversion | $CH_4$ or $C_2H_6$ | 2.83% | 84.84% | 1.40% | 77.42% | 86.85% |
| % Selectivity | Olefins | 67.43% | 82.25% | 81.12% | 88.81% | 80.9% |
| % Yield | Olefins | 1.91% | 69.78% | 1.14% | 68.76% | 69.82% |
| % Selectivity | Carbon Dioxide | 26.78% | 3.99% | 18.88% | 4.11% | 11.51% |
| % Selectivity | Carbon Monoxide | 5.80% | 1.95% | 0.00% | 0.51% | 0.80% |
| % Yield | Carbon Dioxide | 0.76% | 3.38% | 0.27% | 3.18% | 9.99% |
| % Yield | Carbon Monoxide | 0.16% | 1.66% | 0.00% | 0.39% | 0.70% |
| % Selectivity | % $H_2$ Selectivity | 4.49% | 51.07% | 0.00% | 34.76% | 8.99% |
| % Selectivity | % $H_2O$ Selectivity | 95.51% | 48.93% | 100.00% | 75.24% | 91.01% |

TABLE 4

| OTA Composition | | $FeSO_4/CaSO_4$/NaOH | $Fe(NO_3)_3/CaSO_4$/NaOH | $Fe(NO_3)_3$ $CaSO_3$/NaCl | $MnSO_4/CaSO_4$/AMT | $Fe(NO_3)_3/CaSO_4$/NaCl/Pt |
|---|---|---|---|---|---|---|
| Feed | | $C_2H_6$ | $C_2H_6$ | $C_2H_6$ | $C_2H_6$ | $C_2H_6$ |
| Temp, C. | | 840 | 840 | 840 | 840 | 840 |
| GHSV, hr[1] | | 1,200 | 2,400 | 2,400 | 2,400 | 2,400 |
| % Conversion | $CH_4$ or $C_2H_6$ | 85.04% | 83.20% | 83.77% | 82.53% | 86.85% |
| % Selectivity | Olefins | 83.97% | 86.85% | 87.79% | 86.36% | 38.47% |
| % Yield | Olefins | 71.40% | 72.26% | 73.54% | 71.27% | 79.03% |
| % Selectivity | Carbon Dioxide | 6.18% | 4.03% | 2.98% | 1.32% | 37.33% |
| % Selectivity | Carbon Monoxide | 1.36% | 1.42% | 1.29% | 0.90% | 0.12% |
| % Yield | Carbon Dioxide | 5.26% | 3.35% | 2.50% | 1.09% | 0.06% |
| % Yield | Carbon Monoxide | 1.15% | 1.18% | 1.08% | 0.74% | 0.05% |
| % Selectivity | % $H_2$ Selectivity | 29.32% | 26.96% | 29.72% | 74.99% | 0.02% |
| % Selectivity | % $H_2O$ Selectivity | 70.68% | 73.04% | 70.28% | 25.01% | 78.26% |

Table 5 demonstrates the OTA life for a material prepared from Fe(NO3)3, $CaSO_4$ and NaCl in Example 3 over 134 redox ODH cycles.

TABLE 5

| Cycle Number | | 5 | 60 | 65 | 125 | 138 |
|---|---|---|---|---|---|---|
| Feed | | $C_2H_6$ | $C_2H_6$ | $C_2H_6$ | $C_2H_6$ | $C_2H_6$ |
| Temp, C. | | 825 | 825 | 840 | 840 | 840 |
| GHSV, hr[1] | | 3,600 | 3,600 | 3,600 | 3,600 | 2,400 |
| % Conversion | $CH_4$ or $C_2H_6$ | 84.70% | 85.02% | 85.26% | 85.52% | 90.71% |
| % Selectivity | Olefins | 88.18% | 88.13% | 87.11% | 86.01% | 81.41% |
| % Yield | Olefins | 74.69% | 74.92% | 74.27% | 73.55% | 73.85% |
| % Selectivity | Carbon Dioxide | 1.67% | 0.90% | 2.63% | 3.87% | 6.33% |
| % Selectivity | Carbon Monoxide | 1.13% | 1.96% | 1.34% | 1.62% | 2.01% |
| % Yield | Carbon Dioxide | 1.42% | 0.77% | 2.24% | 3.31% | 5.74% |
| % Yield | Carbon Monoxide | 0.96% | 1.67% | 1.15% | 1.38% | 1.83% |
| % Selectivity | % $H_2$ Selectivity | 61.63% | 48.86% | 46.40% | 40.05% | 30.28% |
| % Selectivity | % $H_2O$ Selectivity | 38.37% | 51.14% | 53.60% | 59.95% | 69.72% |

DISCUSSION

In all of the experiments, the product gas had a slight smell of $H_2S$, indicating that some of the $CaSO_4$ had been reduced by the hydrocarbon. In addition, CaS was detected by XRD in samples that were thoroughly reduced by hydrogen. These results indicate the surprising effect of the addition of metal compounds selected from Groups 3 to 14 on $CaSO_4$, thereby significantly enhancing its use as an oxygen carrier for reaction (3), including for OCM and ODH of saturated hydrocarbons to unsaturated hydrocarbons.

Long term commercial application of these metal-catalyzed $CaSO_4$ systems is possible by addition of low levels of sulfur-containing compounds such as $H_2S$, $SO_2$, $SO_3$ and organosulfur compounds to maintain the activity of the systems. In particular, $H_2S$ is a common additive to commercial ethane steam cracker feeds.

While $CaSO_4$ has been demonstrated in the Examples as suitable for the present invention, any sulfate salt of an alkali or alkaline earth metal should also be further activated as an OTA by the teachings of the present invention. Similar results are expected for sulfite salts, bisulfite salts and metabisulfite salts as OTAs. Similarly, the manganese and iron salts shown in the Examples as activating the $CaSO_4$ are merely exemplary of many other suitable elements such as, for example, those of Groups 3 to 14 of the periodic table, such as, but not limited to, Mo, Ti, V, Pr, Cu and La.

While sodium, ammonium metatungstate and platinum were shown in the examples as co-promoters in increasing the selectivity of the sulfate salt OTAs, other promoters may be used and include boron, salts of tungstic acid and common alkali and alkaline earth metal halides.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the invention. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A composition comprising:

(a) 10 to 90 wt % $CaSO_4$;

(b) 1 to 85 wt % of a total of W and at least one of Fe and/or Mn; and (c) 1 to 10 wt % of an alkali metal salt, wherein the composition is capable of oxidative dehydrogenation of a saturated hydrocarbon feed and of OCM.

2. The composition according to claim 1, wherein (b) is W and Fe.

3. The composition according to claim 1, wherein (b) is W and Mn.

4. The composition according to claim 1, wherein (b) is W, Fe and Mn.

5. The composition according to claim 1, wherein (b) is W and Fe, and (c) is an alkali metal halide.

6. The composition according to claim 1, wherein (b) is W and Fe, and (c) is an alkali metal hydroxide.

7. The composition according to claim 1, wherein (b) is W and Mn, and (c) is an alkali metal halide.

8. The composition according to claim 1, wherein fb) is W and Mn, and (c) is an alkali metal hydroxide.

9. The composition according to claim 1, wherein fb) is W, Fe and Mn, and fc) is an alkali metal halide.

10. The composition according to claim 1, wherein (b) is W, Fe and Mn, and (c) is an alkali metal hydroxide.

11. The composition according to claim 1, wherein the composition is in contact with a saturated hydrocarbon feed gas containing 1 to 100,000 ppm of a sulfur containing compound selected from the group consisting of $H_2S$, $SO_2$ or $SO_3$.

* * * * *

UNITED STATES PATENT AND TRADEMARK OFFICE
CERTIFICATE OF CORRECTION

PATENT NO. : 11,104,625 B1
APPLICATION NO. : 16/877992
DATED : August 31, 2021
INVENTOR(S) : John A. Sofranko It is certified that error appears in the above-identified patent and that said Letters Patent is hereby corrected as shown below:

In the Claims

Column 44 Line 21 In Claim 8 – please replace “wherein fb)” with --wherein (b)--;

Column 44 Line 25 In Claim 9 – please replace “wherein fb)” with --wherein (b)--; and Column 44 Line 26 In Claim 9 – please replace “and fc)” with --and (c)--.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*